(12) United States Patent
Lui et al.

(10) Patent No.: US 12,059,681 B2
(45) Date of Patent: *Aug. 13, 2024

(54) DEVICES, SYSTEMS, METHODS, AND KITS FOR RECEIVING A SWAB

(71) Applicant: Labrador Diagnostics, LLC, Wilmington, DE (US)

(72) Inventors: Clarissa Lui, Menlo Park, CA (US); Elizabeth A. Holmes, San Francisco, CA (US)

(73) Assignee: Labrador Diagnostics, LLC, Wilmington, DE (US)

( * ) Notice: Subject to any disclaimer, the term of this patent is extended or adjusted under 35 U.S.C. 154(b) by 15 days.

This patent is subject to a terminal disclaimer.

(21) Appl. No.: 16/524,604

(22) Filed: Jul. 29, 2019

(65) Prior Publication Data
US 2020/0023353 A1    Jan. 23, 2020

Related U.S. Application Data

(63) Continuation of application No. 15/041,488, filed on Feb. 11, 2016, now Pat. No. 10,391,496, which is a (Continued)

(51) Int. Cl.
*C12M 3/00* (2006.01)
*A61B 10/00* (2006.01)
(Continued)

(52) U.S. Cl.
CPC .......... *B01L 3/508* (2013.01); *A61B 10/0096* (2013.01); *B01L 3/5029* (2013.01);
(Continued)

(58) Field of Classification Search
CPC ...................................................... B01L 3/50
See application file for complete search history.

(56) References Cited

U.S. PATENT DOCUMENTS

| 4,683,195 A | 7/1987 | Mullis et al. |
| 4,756,884 A | 7/1988 | Hillman et al. |

(Continued)

FOREIGN PATENT DOCUMENTS

| JP | H11142400 A | 5/1999 |
| JP | 2011069778 A | 4/2011 |

(Continued)

OTHER PUBLICATIONS

Office Action dated Jul. 8, 2015 for U.S. Appl. No. 14/479,241.
(Continued)

*Primary Examiner* — Nathan A Bowers
(74) *Attorney, Agent, or Firm* — Sterne, Kessler, Goldstein & Fox P.L.L.C.

(57) ABSTRACT

Methods, devices, systems, and kits useful for the collection and analysis of samples obtained by swabs are disclosed. Swab containers configured for receiving a swab containing a sample; cartridges for holding one or more of: a swab container, a swab, assay units, pipette tips, vessels, transport units, and implements; systems (which may include a sample processing device); kits; and methods for their use are disclosed. A swab container may include an entry port; an assay chamber having an assay port; a conduit comprising an interior channel connecting the entry port; and an interior channel providing fluidic communication between the entry port and assay chamber. An interior channel may be configured to squeeze a portion of a swab placed in or through the conduit. A cartridge may include a cartridge frame configured to receive one or more of swab containers, assay units, transport units, pipette tips, vessels or implements.

27 Claims, 13 Drawing Sheets

Related U.S. Application Data continuation of application No. PCT/US2014/054419, filed on Sep. 5, 2014.

(60) Provisional application No. 61/885,467, filed on Oct. 1, 2013, provisional application No. 61/879,664, filed on Sep. 18, 2013, provisional application No. 61/874,976, filed on Sep. 6, 2013.

(51) Int. Cl.
- *B01L 3/00* (2006.01)
- *G01N 1/02* (2006.01)
- *G01N 1/10* (2006.01)
- *B01L 1/00* (2006.01)

(52) U.S. Cl.
CPC ............... *G01N 1/02* (2013.01); *G01N 1/10* (2013.01); *A61B 10/007* (2013.01); *B01L 1/52* (2019.08); *B01L 2200/026* (2013.01); *B01L 2200/10* (2013.01); *B01L 2300/0627* (2013.01); *B01L 2300/0832* (2013.01); *B01L 2300/087* (2013.01); *B01L 2300/123* (2013.01); *G01N 2001/028* (2013.01)

(56) References Cited

U.S. PATENT DOCUMENTS

| | | |
|---|---|---|
| 4,803,048 A | 2/1989 | Nason |
| 5,353,803 A * | 10/1994 | Cerra ............... A61B 10/0096 206/569 |
| 6,379,929 B1 | 4/2002 | Burns et al. |
| 6,468,474 B2 | 10/2002 | Bachand et al. |
| 6,524,530 B1 | 2/2003 | Igarashi et al. |
| 6,949,377 B2 | 9/2005 | Ho |
| 7,494,791 B2 | 2/2009 | Goel |
| 7,544,324 B2 | 6/2009 | Tung et al. |
| 8,088,593 B2 | 1/2012 | Burd et al. |
| 8,158,430 B1 | 4/2012 | Roy et al. |
| 8,278,091 B2 | 10/2012 | Rutter et al. |
| 8,380,541 B1 | 2/2013 | Holmes |
| 8,435,738 B2 | 5/2013 | Holmes |
| 9,131,884 B2 | 9/2015 | Holmes et al. |
| 2002/0004019 A1 | 1/2002 | Bachand et al. |
| 2003/0064526 A1 | 4/2003 | Niedbala et al. |
| 2003/0180961 A1 | 9/2003 | Knezevic et al. |
| 2005/0084842 A1 | 4/2005 | Amanda |
| 2005/0100937 A1 | 5/2005 | Holmes |
| 2005/0220668 A1 | 10/2005 | Coville |
| 2006/0019274 A1 | 1/2006 | Goel |
| 2006/0074063 A1 | 4/2006 | Fernandez-Pol |
| 2006/0257993 A1 | 11/2006 | McDevitt et al. |
| 2006/0264780 A1 | 11/2006 | Holmes et al. |
| 2006/0264782 A1 | 11/2006 | Holmes et al. |
| 2007/0154922 A1 | 7/2007 | Collier et al. |
| 2007/0224084 A1 | 9/2007 | Holmes et al. |
| 2007/0264629 A1 | 11/2007 | Holmes et al. |
| 2008/0153096 A1 | 6/2008 | Witty et al. |
| 2009/0019953 A1 | 1/2009 | Bommarito et al. |
| 2009/0030342 A1 | 1/2009 | Flanigan et al. |
| 2009/0081648 A1 | 3/2009 | Wangh |
| 2009/0088336 A1 | 4/2009 | Burd et al. |
| 2009/0143235 A1 | 6/2009 | Drmanac et al. |
| 2009/0203085 A1 | 8/2009 | Kum et al. |
| 2010/0015634 A1 | 1/2010 | VanDine et al. |
| 2010/0077843 A1 | 4/2010 | Doraisamy et al. |
| 2010/0111773 A1 | 5/2010 | Pantelidis |
| 2011/0093249 A1 | 4/2011 | Holmes et al. |
| 2011/0207617 A1 | 8/2011 | Faham et al. |
| 2012/0070831 A1 | 3/2012 | Johnson |
| 2012/0309636 A1 | 12/2012 | Gibbons et al. |
| 2013/0074614 A1 | 3/2013 | Holmes et al. |
| 2013/0078149 A1 | 3/2013 | Holmes et al. |
| 2013/0078624 A1 | 3/2013 | Holmes et al. |
| 2013/0078625 A1 | 3/2013 | Holmes et al. |
| 2013/0078733 A1 | 3/2013 | Holmes et al. |
| 2013/0079599 A1 | 3/2013 | Holmes et al. |
| 2013/0080071 A1 | 3/2013 | Holmes |
| 2013/0243794 A1 | 9/2013 | Hauser |
| 2013/0244241 A1 | 9/2013 | Fabra et al. |
| 2014/0045170 A1 | 2/2014 | Patel et al. |
| 2014/0057255 A1 | 2/2014 | Holmes |
| 2014/0057770 A1 | 2/2014 | Holmes et al. |
| 2014/0073043 A1 | 3/2014 | Holmes |
| 2014/0081665 A1 | 3/2014 | Holmes |
| 2014/0170678 A1 | 6/2014 | Kasdan et al. |
| 2014/0170688 A1 | 6/2014 | Matje et al. |
| 2014/0170735 A1 | 6/2014 | Holmes |
| 2014/0229955 A1 | 8/2014 | Holmes et al. |
| 2014/0234949 A1 | 8/2014 | Wasson et al. |
| 2014/0272938 A1 | 9/2014 | Loo et al. |
| 2014/0287955 A1 | 9/2014 | Wende et al. |
| 2014/0295439 A1 | 10/2014 | Patel |
| 2014/0295440 A1 | 10/2014 | Belhocine et al. |
| 2014/0295447 A1 | 10/2014 | Hayashizaki et al. |
| 2014/0296089 A1 | 10/2014 | Holmes et al. |
| 2014/0308661 A1 | 10/2014 | Holmes et al. |
| 2014/0335505 A1 | 11/2014 | Holmes |
| 2014/0342371 A1 | 11/2014 | Holmes |
| 2015/0072338 A1 | 3/2015 | Holmes |
| 2015/0072362 A1 | 3/2015 | Lui et al. |
| 2015/0072889 A1 | 3/2015 | Lui et al. |
| 2015/0076008 A1 | 3/2015 | Athanasiou et al. |
| 2015/0299777 A1 | 10/2015 | Patel et al. |
| 2016/0070884 A1 | 3/2016 | Lui et al. |
| 2016/0175838 A1 | 6/2016 | Lui |
| 2016/0243543 A1 | 8/2016 | Lui et al. |

FOREIGN PATENT DOCUMENTS

| | | |
|---|---|---|
| RU | 2147123 C1 | 3/2000 |
| WO | 1999004043 A1 | 1/1999 |
| WO | 2004055198 A2 | 7/2004 |
| WO | 2004061418 A2 | 7/2004 |
| WO | 2008050254 A1 | 5/2008 |
| WO | 2008115632 A2 | 9/2008 |
| WO | 2012025729 A1 | 3/2012 |
| WO | 2010090857 | 6/2012 |
| WO | 2013006312 A2 | 3/2013 |
| WO | 2013052318 A1 | 4/2013 |
| WO | 2015035256 A2 | 3/2015 |
| WO | 2015035260 A1 | 3/2015 |

OTHER PUBLICATIONS

Office Action dated Aug. 27, 2015 for U.S. Appl. No. 14/479,190.
Office Action dated Sep. 1, 2017 for U.S. Appl. No. 15/041,421.
Office Action dated Sep. 24, 2015 for U.S. Appl. No. 14/479,245.
Plebani. Evaluating and using innovative technologies: a lesson from Theranos? Clin Chem Lab Med. Jun. 2015;53(7):961-2.
Preliminary Amendment dated Feb. 12, 2016 for U.S. Appl. No. 15/042,909.
Preliminary Amendment dated Apr. 29, 2016 for U.S. Appl. No. 15/041,421.
Ramsey L. Theranos has a week to respond to the searing report about its business. Business Insider. Feb. 5, 2016. http://www.businessinsider.com/theranos-response-to-cms-2016-2.
Rappleye E. Theranos gets extension to fix issues following CMS investigation. Becker's Hospital Review. Feb. 8, 2016. http://www.beckershospitalreview.com/hospital-management-adminstration/theranos-gets-extension-to-fix-Issues-following-cms-investigation.html.
Roskos et al. Simple System for Isothermal DNA Amplification Coupled to Lateral Flow Detection. PLoS One. Jul. 26, 2013;8(7):e69335. Print 2013.
Sahni et al. Reverse transcription loop-mediated isothermal amplification (RT-LAMP) for diagnosis of dengue. Med J Armed Forces India. Jul. 2013; 69(3):246-53. doi: 10.1016/j.mjafi.2012.07.017. Epub Dec. 1, 2012.
The International Search Report and Written Opinion dated May 28, 2015 for PCT/US2014/054419.

(56) References Cited

OTHER PUBLICATIONS

Voudoukis et al., 2011, Med Sci Monit, 17(4), pp. 185-188.
Wang Y. et al. "Methicillin resistant *Staphyloccus aureus* infection: a case report and literature review". Zhonghua Jie He Hu Xi Za Zhi, Sep. 2009; 32(9):pp. 665-659, abstract.
World Health Organization (WHO) Guide to Field Operations, Oct. 2006, pp. 1-80.
Written Opinion and International Search Report dated Dec. 18, 2014 for PCT/US2014/054424.
Zimmerman O et al. C-reactive protein serum levels as an early predictor of outcome in patients with pandemic H1N1 influenza A virus infection. BMC Infect Dis. Oct. 4, 2010;10:288.
510(k) Substantial Equivalence Determination Decision Summary dated Jul. 16, 2015 for "Theranos Herpes Simplex Virus-1 (HSV-1) IgG Assay".
510(k) Substantial Equivalence Determination issued for "Theranos Herpes Simplex Virus-1 IgG Assay" by the FDA on Jul. 7, 2015.
Advisory Action dated Nov. 10, 2015 for U.S. Appl. No. 14/479,190.
Advisory Action dated Sep. 25, 2015 for U.S. Appl. No. 14/479,241.
Anders et al., Am Journal Med Hyg 87(1), 2012, pp. 165-170.
AppliedBiosystems StepOne Real-Time PCR System Manual, Rev. 2010.
B. Rodriguez-Sanchez et al. Improved Diagnosis for Nine Viral Diseases Considered as Notifiable by the World Organization for Animal Health. Transbound Emerg Dis. Aug. 2008; 55(5-6): 215-25.
Chantreuil J. et al. "Artial chaotic tachycardia during a respiratory tract infection due to NL63 coronavirus". Arch Pediatr, Mar. 2013; 20(3):pp. 278-281, abstract.
Chin et al. Low-Cost Microdevices for Point-of-Care Testing. Biological and Medical Physics, Biomedical Engineering pp. 3-21. Oct. 12, 2012.
Craw et al. Isothermal nucleic acid amplification technologies for point-of-care diagnostics: a critical review, Lab On a Chip, vol. 12, No. 14, Jul. 1, 2012.
Dapat I.C. et al. Genetic characterization of human influenza viruses in the pandemic (2009-2010) and post-pandemic (2010-2011) periods in Japan. PLoS One, 2012; 7(6):e36455.
Diamandis. Theranos phenomenon: promises and fallacies. Clin Chem Lab Med. Jun. 2015;53(7):989-93.
Fuller K. Centers for Medicare and Medicaid Services (CMS). Condition Level Deficiencies Notice—Immediate Jeopardy. Notice to Theranos, Inc. director Dr. Sunil Dhawan. Jan. 25, 2016. https://cdn2.vox-cdn.com/uploads/chorus_asset/file/5969923/Theranos_Inc_Cover_Letter_01-25-2016.0.pdf.
Gill, et al. Nucleic acid isothermal amplification technologies: a review. Nucleosides, Nucleotides and Nucleic Acids. Mar. 2008; 27(3):224-43.
Havlickova M et al. Influenza virus detection in clinical specimens. Abstract. Acta Virol. Sep. 1990;34(5):449-56.
Horton et al. Engineering hybrid genes without the use of restriction enzymes: gene splicing byoverlap extension. Gene, Elsevier, Amsterdam, NL, vol. 77, No. 1, Apr. 15, 1989, pp. 61-68.
Hung et al. Effect of clinical and virological parameters on the level of neutralizing antibody against pandemic influenza A virus H1N1 2009. Clin Infect Dis. Aug. 1, 2010;51(3):274-9.
Jannetto et al. Real-Time Detection of Influenza A, Influenza B, and Respiratory Syncytial Virus A and B in Respiratory Specimens by Use of Nanoparticle Probes. J Clin Microbiol. Nov. 2010;48(11):3997-4002. Epub Sep. 8, 2010.
Kautner et al., Journal of Pediatrics, 1997, 131, pp. 516-524.
Kimura Y et al. Tail variation of the folding primer effects the SmartAmp2 process differently. Biochem Biophys Res Commun. Jun. 12, 2009;383(4):455-9.
Li, Peng. (2012) Microfluidics for IVD: In Pursuit of the Holy Grail. J Bioengineer & Biomedical Sci S8:e001.
Loria K. More skeptical than ever: Experts respond to the government's warning letter to Theranos. Jan. 28, 2016. Tech Insider. http://www.techinsider/io/how-bad-the-cms-letter-to-theranos-really-is-2016-1.
Lounsbury et al., Lab Chip, 2013, 13, pp. 1384-1393.
Luk F.O. et al. A case of dengue maculopathy with spontaneous recovery. Case Rep Ophthalmol, Jun. 8, 2013;4(2):pp. 28-33.
Mahony et al. Molecular diagnosis of respiratory virus infections. Crit Rev Clin Lab Sci. Sep.-Dec. 2011;48(5-6):217-49.
Metzgar D. et al. Single assay for simultaneous detection and differential identification of human and avian influenza virus types, subtypes, and emergent variants. PLoS One. Feb. 3, 2010;5(2):e8995.
Notice of Allowance dated Dec. 8, 2015 for U.S. Appl. No. 14/479,190.
Notice of Allowance dated Jun. 6, 2016 for U.S. Appl. No. 14/479,245.
Notice of Allowance dated Aug. 22, 2016 for U.S. Appl. No. 14/479,241.
Obryadina A.P. et al, "Avidnost antitel v diagnostike infektsionnykh zabolevaniy" Laboratornaya diagnostika infektsionnykh zabolevaniy, 2007, No. 4, p. 3-7 (with English translation).
Office Action dated Jan. 29, 2015 for U.S. Appl. No. 14/479,241.
Office Action dated Jan. 5, 2018 for U.S. Appl. No. 15/041,488.
Office Action dated Oct. 9, 2018 for U.S. Appl. No. 15/041,488.
Office Action dated Nov. 12, 2014 for U.S. Appl. No. 14/479,245.
Office Action dated Nov. 14, 2016 for U.S. Appl. No. 15/042,909.
Office Action dated Nov. 19, 2015 for U.S. Appl. No. 14/604,194.
Office Action dated Nov. 8, 2016 for U.S. Appl. No. 14/604,194.
Office Action dated Dec. 29, 2016 for U.S. Appl. No. 15/041,421.
Office Action dated Feb. 12, 2015 for U.S. Appl. No. 14/479,190.
Office Action dated Feb. 24, 2016 for U.S. Appl. No. 14/479,245.
Office Action dated Mar. 21, 2019 for U.S. Appl. No. 15/041,488.
Office Action dated Mar. 29, 2017 for U.S. Appl. No. 14/789,904.
Office Action dated Mar. 8, 2016 for U.S. Appl. No. 14/604,194.
Office Action dated Apr. 18, 2016 for U.S. Appl. No. 14/479,241.
Office Action dated Apr. 26, 2018 for U.S. Appl. No. 15/042,909.
Office Action dated Apr. 28, 2016 for U.S. Appl. No. 15/042,909.
Office Action dated Apr. 3, 2015 for U.S. Appl. No. 14/479,245.
Office Action dated Apr. 3, 2017 for U.S. Appl. No. 14/604,194.
Office Action dated Jun. 14, 2017 for U.S. Appl. No. 15/042,909.
Office Action dated Jun. 8, 2017 for U.S. Appl. No. 15/041,488.

\* cited by examiner

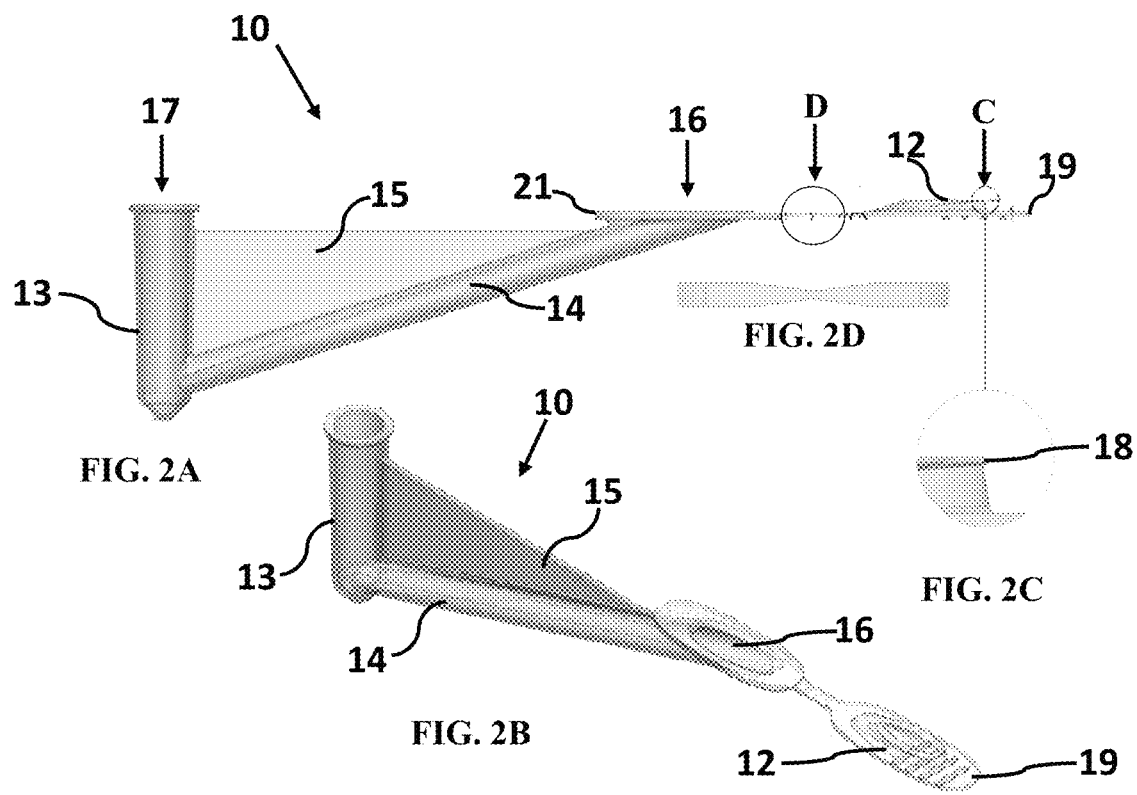
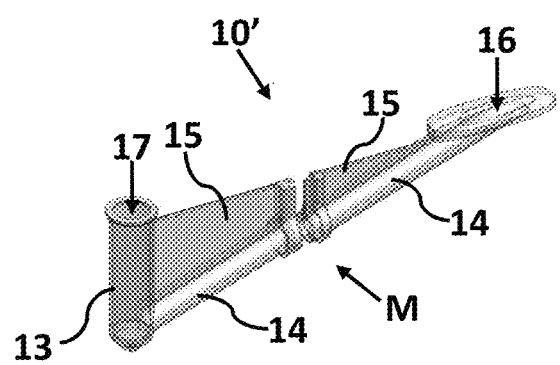

DEVICES, SYSTEMS, METHODS, AND KITS FOR RECEIVING A SWAB

BACKGROUND

The collection of fluid or tissue samples is often required in the diagnosis and treatment of subjects suffering from many diseases and medical conditions. Sample collection from the mouth, nose, throat, and other locations may be accomplished by brushing or scraping a body surface with a swab. For example, some diseases may be detected by analysis of swabs, or fluid obtained from swabs, such as throat swabs, nasal swabs, cheek swabs, or other swabs, such as, influenza and other respiratory disorders; tuberculosis; bacterial infections such as diphtheria, whooping cough, and those caused be caused by *staphylococcus, streptococcus, pneumococcus*, and other bacteria; viral infections, such as, e.g., adenovirus infections; some genetic diseases caused by or related to a subject's genetic characteristics; and other diseases and disorders. Diseases may also be detected by analysis of urine samples, and other clinical samples.

Analysis of the sample typically requires that the collected fluid or tissue be transferred from the swab to a vessel, slide, or analysis device. However, such transfer is often incomplete, and loss or degradation of the sample may occur before analysis. Accordingly, improved swabbing methods and swab collection devices are required.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Methods, devices, systems, and kits useful for the collection and analysis of samples obtained by swabs are disclosed.

Devices for receiving a swab after the swab has contacted a subject and obtained a sample of fluid, tissue, secretion, excretion, or combinations thereof, are disclosed. Cartridges configured to receive such devices, and, in embodiments, to further receive sample collection vessels, reagent vessels, implements, or waste vessels, or combinations thereof, are disclosed. Systems including such devices, or cartridges, or both, are disclosed; such systems may further include sample processing devices (e.g., automatic sample processing devices), reagents, implements, and other elements, are disclosed. Kits including such devices and cartridges; or such devices, cartridges, and swabs; or such devices, cartridges, and vessels (e.g., reagent vessels, waste vessels, or other vessels); or such devices, cartridges, and an implement (e.g., a cuvette); or combinations thereof, are disclosed.

In embodiments, Applicants disclose containers that are configured to receive a swab (swab containers). In embodiments, Applicants disclose cartridges configured to receive a swab container, and, in embodiments, configured to further receive implements (e.g., cuvettes) or vessels, such as sample collection vessels, reagent vessels, mixing vessels, and waste vessels, or both implements and vessels. In embodiments, Applicants disclose systems comprising one or more of swab containers, cartridges, vessels, implements, and sample processing devices. In embodiments, Applicants disclose methods for collecting samples, and methods for analyzing samples, using the swab containers, cartridges, and systems disclosed herein. In embodiments, Applicants disclose kits comprising one or more of swabs, swab containers, cartridges, vessels, and implements useful for collecting samples and for analyzing samples.

In embodiments, Applicants provide a container for receiving a swab, comprising an entry port, said entry port configured to receive a swab having a handle; an assay chamber having an assay port, said assay chamber being configured to receive at least a portion of a swab; a conduit comprising an interior channel connecting said entry port with said assay chamber, said conduit being configured to accept at least a portion of said swab handle therein; wherein said conduit provides fluidic communication between said entry port and said assay chamber effective that passing a swab through said entry port into said conduit allows at least a portion of the swab to be placed within said assay chamber.

In embodiments, a swab container may comprise a conduit interior channel that is configured to squeeze a portion of a swab placed in or through said conduit interior channel portion adjacent to said assay chamber. In embodiments, a swab container may comprise a conduit interior channel comprising interior dimensions, wherein said interior dimension near said entry port is greater than said interior dimension near said assay chamber. In embodiments, a conduit interior channel may comprise a cross-section having a cross-sectional shape selected from round, oval, square, rectangular, rhomboid, and triangular. In embodiments, a conduit may connect with an assay chamber at a contact angle, wherein said contact angle comprises between about 10° to about 90°, or between about 40° to about 85°, or between about 70° to about 80°. In embodiments, a contact angle may comprise an angle of between about 70° to about 80°. In embodiments, a swab container assay chamber may have a cross-sectional dimension, wherein said cross-sectional dimension comprises between about 3 millimeters (mm) to about 30 mm, or between about 4 mm to about 20 mm, or between about 5 mm to about 15 mm. In embodiments, a swab container may have an assay chamber having a cross-sectional dimension, wherein said cross-sectional dimension comprises between about 3 millimeters (mm) to about 30 mm, or between about 4 mm to about 20 mm, or between about 5 mm to about 15 mm. In embodiments, a conduit interior channel may comprise a length, wherein said length is between about 50 millimeters (mm) and about 150 mm. In embodiments, a swab container may have a contact angle of between about 70° to about 80°, and a conduit interior channel having a length of between about 50 millimeters (mm) and about 150 mm.

A swab container as disclosed herein may have a cover, e.g. a cover for an entry port, a cover for an assay port, or both. In embodiments, such a cover may be a pierceable cover. In embodiments, a swab container may comprise a cover that is flexibly connected to an assay chamber, assay port, conduit, or entry port, and the cover may be configured to cover an assay port or an entry port in a first position and to be disposed away from an assay port or an entry port in a second position.

In embodiments, a swab container interior channel may comprise a length that is sufficient to contain at least a portion of a swab handle when a swab having a handle is disposed within an interior channel of the conduit. A conduit of a swab container as disclosed herein may connect with an assay chamber at a contact angle.

A swab container as disclosed herein may contain a reagent for bathing a swab, wherein said reagent for bathing a swab is effective to receive sample material from said swab into said reagent.

A swab container may comprise a conduit having a plurality of interior channels or a plurality of conduits each of which comprise at least one interior channel, wherein each of said interior channels provides fluidic communication between an entry port and said assay chamber effective that passing a swab through said entry port into said conduit allows at least a portion of the swab to be placed within said assay chamber. In embodiments, a swab container having a conduit having a plurality of interior channels may connect with an entry port effective that one entry port is in fluidic communication with more than one interior channel. In embodiments, a swab container having a conduit having a plurality of interior channels may connect with one or more entry ports effective that each interior channel is in fluidic communication with a single entry port. In embodiments, a swab container may have a plurality of interior channels each providing fluidic communication between an entry port and an assay chamber effective that passing a swab through the entry port into a conduit allows at least a portion of the swab to be placed within said assay chamber, wherein the plurality of interior channels are selected from i) two or more interior channels within a conduit; ii) two or more conduits each having an interior channel; and iii) combinations thereof. In embodiments, a swab container may have more than one assay chamber. In embodiments, a swab container with more than one assay chamber may have one, or may have more than one, conduit; and may have one, or may have more than one, interior channel in the one, or in the more than one, conduit.

An entry port, conduit with at least one interior channel, and assay chamber of a swab container as disclosed herein are configured to allow placement of a swab through an entry port and interior chamber and into an assay chamber. In embodiments, a swab may comprise a handle, and placement of a swab through an entry port and interior chamber and into an assay chamber may comprise placement of a swab and its handle into an assay chamber, or may comprise placement of a portion of a swab into an assay chamber, and placement of a swab handle to a position near to an assay chamber. In embodiments, an entry port, interior channel, assay chamber, or combinations thereof, may be configured to snugly hold a swab, including a swab with a handle, or portions of these. Thus, in embodiments, while allowing entry and positioning of a swab within a swab container, an entry port, interior channel, assay chamber, or combinations thereof, may be sized or shaped, or both, to hold a swab in place within a swab container. In embodiments, such a snug fit may apply to some or all portions of a swab, or a swab handle, or combinations thereof.

A swab container as disclosed herein may be made with any suitable material. For example, a swab container may comprise a material selected from glass, plastic, polymer, rubber, metal, composite, or other material, or combination of materials. In embodiments, a swab container may be made from, e.g., polypropylene, polycarbonate, polystyrene, polyurethane, polyethylene, polyacrylamide, polyacrylate, polymethacrylate, polymethylmethacrylate (PMMA), poly (4-methylbutene), other acrylic, polydimethysiloxanes (PDMS), polyvinylchloride (PVC), poly(vinyl butyrate) polysulfone, acrylonitrile-butadiene-styrene (ABS), poly (ethylene terephthalate), a fluorocarbon polymer (e.g., poly-tetrafluoroethylene (PTFE or Teflon®)), nylon, a co-polymer, or combinations thereof.

Applicants disclose cartridges, where the cartridges may be configured to receive a swab container. Accordingly, in embodiments, Applicants disclose a cartridge comprising: a cartridge frame; and a swab container, the swab container comprising: an entry port configured to receive a swab having a handle; an assay chamber having an assay port, said assay chamber being configured to receive a swab; an assay chamber having an assay port, said assay chamber being configured to receive a swab; a conduit comprising an interior channel connecting said entry port with said assay chamber, said conduit being configured to accept at least a portion of said swab handle therein; wherein said conduit provides fluidic communication between said entry port and said assay chamber effective that passing said swab through said entry port into said conduit allows a swab to be placed within said assay chamber, wherein said cartridge is configured to receive said swab container. In embodiments, a cartridge for holding reagents comprises at least one cartridge frame, and a swab container; such a cartridge frame is configured to receive a swab container, and such a swab container is configured to receive a swab. In embodiments, a swab container comprises an entry port configured to receive a swab having a handle; an assay chamber having an assay port, said assay chamber being configured to receive a swab; a conduit comprising an interior channel connecting said entry port with said assay chamber, said conduit being configured to accept at least a portion of said swab handle therein; wherein said conduit provides fluidic communication between said entry port and said assay chamber effective that passing said swab through said entry port into said conduit allows a swab to be placed within said assay chamber.

In embodiments of the cartridges disclosed herein, the assay chamber of the swab container contains a reagent for bathing a swab, wherein said reagent for bathing a swab is effective to receive sample material from said swab into said reagent. In embodiments of the cartridges disclosed herein, the cartridge frame is configured to receive a vessel, a pipette tip, a transport unit, an implement, or combinations thereof. In embodiments of the cartridges disclosed herein, the vessels may comprise one or more of a reagent vessel, a mixing vessel, a waste vessel, and a sample collection vessel. In embodiments of the cartridges disclosed herein, a vessel may comprise a reagent vessel containing a reagent. In embodiments, an implement may comprise a cuvette. In embodiments of the cartridges disclosed herein, the swab container may comprise a cover configured to cover an entry port, a cover configured to cover an assay port, or both. In embodiments of the cartridges disclosed herein, such a cover may be a pierceable cover. In embodiments of the cartridges disclosed herein, such a cover may be flexibly connected to the swab container.

Accordingly, in embodiments, Applicants disclose a cartridge comprising: a cartridge frame comprising a plurality of receptacles, wherein said receptacles comprise: one or more receptacles selected from a receptacle configured to receive a sample collection vessel, a receptacle configured to receive a reagent vessel, a receptacle configured to receive an assay unit, a receptacle configured to receive a mixing vessel, a receptacle configured to receive a waste vessel, a receptacle configured to receive a pipette tip, a receptacle configured to receive a transport unit, and a receptacle configured to receive an implement; and a swab container receptacle configured to receive a swab container; wherein said swab container comprises an entry port, said entry port configured to receive a swab having a handle; an assay chamber having an assay port, said assay chamber being configured to receive at least a portion of a swab; and a conduit comprising an interior channel connecting said entry port with said assay chamber, said conduit being configured to accept a least a portion of said swab handle therein, wherein said conduit provides fluidic communication between said entry port and said assay chamber effective that passing a swab through said entry port into said conduit allows the swab to be placed within said assay chamber.

In embodiments, a cartridge as disclosed herein may comprise a swab container in a swab container receptacle. In embodiments, a cartridge as disclosed herein may comprise a swab container including a reagent contained therein, the swab container being disposed in a swab container receptacle. In embodiments, a cartridge as disclosed herein may comprise an assay chamber containing a reagent for bathing a swab, wherein the reagent for bathing a swab is effective to receive sample material from a swab into the reagent. In embodiments, a cartridge as disclosed herein may comprise one or more of a sample collection vessel, a reagent vessel, an assay unit, a mixing vessel, a waste vessel, a pipette tip, a transport unit, and an implement disposed in one or more receptacles. In embodiments, a reagent vessel may comprise a reagent contained within said reagent vessel. In embodiments, an implement may comprise a cuvette.

In embodiments, a cartridge may comprise a swab container. In embodiments, a swab container disposed in a cartridge may comprise a conduit interior channel configured to squeeze a portion of a swab placed in or through a portion of the conduit interior channel adjacent to said assay chamber. In embodiments, a swab container disposed in a cartridge may comprise a conduit having a plurality of interior channels or a plurality of conduits each of which comprise at least one interior channel. In embodiments, a swab container disposed in a cartridge may comprise a cover configured to cover said entry port, a cover configured to cover said assay port, or both. In embodiments, such a cover may comprise a pierceable cover. In embodiments, such a cover may comprise a cover that is flexibly connected to the swab container.

In embodiments, a cartridge may be configured to hold a swab container. A cartridge configured to hold a swab container may include a receptacle configured to hold a swab container. In embodiments, a cartridge may be configured to hold a swab container and a sample container. A cartridge configured to hold a swab container and a sample container may include a receptacle configured to hold a swab container, and a receptacle configured to hold a sample container. A swab container held in a receptacle configured to hold a swab container may contain a swab, or may not contain a swab. In embodiments, a cartridge may be configured to hold a swab container, a sample container, and a swab. A cartridge configured to hold a swab container, a sample container, and a swab may include a receptacle configured to hold a swab container, a receptacle configured to hold a sample container, and a receptacle configured to hold a swab. Thus, in embodiments, a cartridge may hold a swab container; a cartridge may hold a sample container; a cartridge may hold a swab container and a sample container; and a cartridge may hold a swab container, a sample container, and a swab. In embodiments, a sample container may hold a sample; and in embodiments, a sample container may be empty (e.g., prior to placing a sample in the sample container). In embodiments, a swab container may hold a swab; and in embodiments, a swab container may be empty (e.g., prior to placing a swab in the swab container). In embodiments, a receptacle configured to hold a swab container may be empty; may hold an empty swab container; or may hold a swab container containing a swab. In embodiments, a receptacle configured to hold a sample container may be empty; may hold an empty sample container; or may hold a sample container containing a sample. In embodiments, a receptacle configured to hold a swab may be empty; or may hold a swab.

In embodiments, a cartridge as disclosed herein may have a lid. A lid may cover the entirety, or may cover only a portion, of the interior of the cartridge. In embodiments, a lid may cover much of the interior of the cartridge, while including an aperture, or a plurality of apertures, where an aperture provides access to an interior portion of the cartridge. In embodiments, for example, an aperture may provide access to a swab container receptacle, or to a swab container held in a swab container receptacle, of the cartridge. In embodiments, for example, an aperture may provide access to a sample container receptacle, or to a sample container held in a sample container receptacle, of the cartridge. In embodiments, for example, an aperture or a plurality of apertures may provide access to a swab container receptacle and a sample container receptacle, or to either or both of a swab container and sample container held in their respective receptacles. In embodiments, such a lid may be removable. In embodiments, such a lid may be attached to the remainder of the cartridge by a hinge or other flexible connection, effective that the lid may be displaced so as to afford access to an interior portion of the cartridge (e.g., to provide access to one or more receptacles) while the lid remains attached to the cartridge. A lid may be configured to move, e.g., to be opened, at any time; for example, in embodiments, a cartridge lid may be opened when the cartridge is outside a sample analysis device. In embodiments, a cartridge lid may be opened when the cartridge is inserted into, or loaded onto, a sample analysis device. In embodiments, a cartridge lid may be opened when the cartridge is on, or within, a sample analysis device.

In embodiments, a cartridge as disclosed herein may include a guide, or rail, or slot, or other feature or features configured to aid in proper insertion of the cartridge into, or of the cartridge onto, a sample analysis device, such as an automatic sample analysis device. Such guides, or rails, or slots, or other features may provide an indication of the proper cartridge orientation for insertion into, or loading onto, a sample analysis device; and may be configured to prevent improper positioning of the cartridge (e.g., where an improper orientation creates a miss-match, or physical barrier, or other impediment, to insertion or loading of the cartridge).

In embodiments, the position of an aperture in a cartridge lid may indicate an orientation of the cartridge; such an indication, for example, may be useful to aid in proper positioning of the cartridge, e.g., when a cartridge is loaded onto, or inserted into, a sample analysis device such as an automatic sample analysis device. For example, where an aperture providing access to a swab container receptacle, or to a swab container held in a swab container receptacle, is positioned at one corner of a substantially square or rectangular cartridge, such position may indicate the proper orientation of the cartridge for insertion into an automatic sample analysis device. For example, the proper position may be that the aperture should be oriented to be at the left-most outer corner of the cartridge, where the portion of the cartridge nearest to the aperture is the proximal portion of the cartridge, and the portion farther from the aperture is the distal portion, so that the orientation with the aperture positioned at the left as the distal portion is inserted into the automatic sample analysis device prior to insertion of the proximal portion, is the proper orientation.

Applicants disclose systems comprising swab containers; systems comprising cartridges configured to receive a swab container or comprising cartridges having swab containers disposed therein; and systems comprising cartridges and sample processing devices. In embodiments, such a system may comprise any swab container, or any cartridge disclosed herein, or both. Accordingly, in embodiments, Applicants disclose a system comprising: a swab; a container for receiving swab, the swab container having an assay chamber, a conduit, and an entry port and being configured to receive at least a portion of the swab in the assay chamber; and a reagent for bathing a swab, the reagent being disposed, at least in part, in the assay chamber, wherein the reagent for bathing a swab is effective to receive sample material from the swab into the reagent. In embodiments, such a system may comprise any cartridge disclosed herein. In embodiments, such a system may comprise a reagent vessel, a waste vessel, a mixing vessel, a sample collection vessel, an assay unit, a pipette tip, a transport unit, an implement, or combinations thereof, disposed in said cartridge. In embodiments, a reagent vessel may comprise a reagent contained therein. In embodiments, an implement may comprise a cuvette.

In embodiments, Applicants disclose such a system, further comprising a sample processing device.

In embodiments, Applicants disclose a system comprising: a swab container, the swab container having an assay chamber, a conduit and an entry port and being configured to receive at least a portion of the swab in the assay chamber; a cartridge, the cartridge comprising a cartridge frame comprising a plurality of receptacles, the receptacles comprising a swab container receptacle configured to receive a swab container, and one or more receptacles selected from a receptacle configured to receive a sample collection vessel, a receptacle configured to receive a reagent vessel, a receptacle configured to receive an assay unit, a receptacle configured to receive a pipette tip, a receptacle configured to receive a transport unit, a receptacle configured to receive an implement, a receptacle configured to receive a mixing vessel, and a receptacle configured to receive a waste vessel; and a sample processing device.

In embodiments, the swab container may contain a reagent for bathing a swab, the reagent being disposed at least in part within the assay chamber, wherein the reagent for bathing a swab is effective to receive sample material from said swab into said reagent. In embodiments, the cartridge may contain a reagent vessel placed in a receptacle of the cartridge, wherein the reagent vessel contains reagent. In embodiments, the cartridge may comprise a waste vessel placed in a receptacle of the cartridge. In embodiments, the cartridge may comprise a sample collection vessel placed in a receptacle of said cartridge. In embodiments, the cartridge may comprise an assay unit placed in a receptacle of said cartridge. In embodiments, the cartridge may comprise a pipette tip placed in a receptacle of said cartridge. In embodiments, the cartridge may comprise a transport unit placed in a receptacle of said cartridge. In embodiments, the cartridge may comprise an implement placed in a receptacle of said cartridge; in embodiments, the implement may be a cuvette; in embodiments, the implement may be a magnet (e.g., a magnetic bar).

Applicants disclose methods of obtaining samples, and methods of analyzing samples, wherein the methods utilize swab containers, cartridges, and systems as disclosed herein.

Accordingly, in embodiments, Applicants disclose a method of obtaining a sample, comprising: providing a system as disclosed herein comprising a swab, a container for receiving a swab, and a reagent, wherein said reagent is disposed within said assay chamber; contacting said swab with a subject effective to obtain sample material on said swab; and placing the swab into said assay chamber by maneuvering the swab through said entry port and conduit into the assay chamber, effective that said sample material on said swab is dispersed into said reagent.

In embodiments, Applicants disclose a method of obtaining a sample from a subject, comprising: contacting a subject with a swab effective to obtain sample material on the swab; and placing the swab into an assay chamber of a swab container, wherein the swab container comprises an entry port, a conduit, and an assay chamber containing a reagent, wherein placing said swab into an assay chamber comprises maneuvering the swab through said entry port and conduit into the assay chamber, effective that said sample material on said swab is dispersed into said reagent. In embodiments, such methods comprise use of swab containers wherein said conduit comprises an interior channel having a constricted portion configured to squeeze the swab when the swab is placed into said assay chamber via said interior channel.

In embodiments, Applicants disclose a method of analyzing a sample obtained from a subject, comprising: contacting a subject with a swab effective to obtain sample material on said swab; placing at least a portion of the swab into an assay chamber of a swab container, wherein the swab container comprises an entry port, a conduit, and an assay chamber containing a reagent, wherein placing at least a portion of the swab into an assay chamber comprises maneuvering the swab through said entry port and conduit into the assay chamber, effective that sample material on said swab is dispersed into said reagent; and analyzing the sample. In embodiments, such methods comprise use of swab containers wherein said conduit comprises an interior channel having a constricted portion configured to squeeze said swab when said swab is placed into said assay chamber via said interior channel. In embodiments, such methods comprise analyzing a sample using a sample processing device, which may be an automated sample processing device.

Applicants disclose kits comprising swabs; swab containers; kits comprising cartridges; kits containing vessels (which may include sample collection vessels), reagents, assay units, pipette tips, transport units, implements, and other elements; and kits comprising combinations thereof.

Accordingly, in embodiments, Applicants disclose a kit for obtaining samples, comprising a container as disclosed herein, and a swab. In embodiments, Applicants disclose a kit for obtaining samples, comprising a cartridge as disclosed herein, and a swab. In embodiments, Applicants disclose a kit for obtaining samples, comprising a swab container as disclosed herein, a cartridge as disclosed herein, and a swab. Applicants disclose a kit for obtaining samples, comprising a swab container as disclosed herein, a cartridge as disclosed herein, and a reagent (which may be in a reagent vessel, in a swab container, or both). Applicants disclose a kit for obtaining samples, comprising a swab container as disclosed herein, a cartridge as disclosed herein, a reagent (which may be in a reagent vessel, in a swab container, or both), and a swab.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIGS. 2A-2E show views of an exemplary swab container. In the embodiment shown in this figure, the swab container has an entry port, a conduit, an assay chamber, and a cover configured for covering the entry port. As shown, a rib may provide structural support to the swab container. FIG. 2A shows a side view, and FIG. 2B shows a top perspective view, while FIG. 2C provides an exploded view of a portion of the cover, and FIG. 2D provides an exploded view of a narrowing which facilitates flexing of the connection between the lip and the cover. FIG. 2E provides an embodiment of a swab container which may be assembled for use from two parts, and which may be dis-assembled after insertion of a swab into a forward and a rear portion; the forward portion may be suitable for placement in a cartridge. The two portions meet and engage each other at the position indicated by the arrow labeled "M".

FIG. 3A provides a side view, and FIGS. 3B and 3C provide cross-sectional views showing the interior channel within the conduit of the swab container. FIG. 3B provides a cross-section taken as indicated by the arrow labeled "B" in FIG. 3A, and FIG. 3C provides a cross-section taken as indicated by the arrow labeled "C" in FIG. 3A. The interior channel is narrower near the assay chamber (shown in FIG. 3B) than near it is near the assay chamber 13 (shown in FIG. 3C).

FIG. 7A shows such a cartridge with the cover closed, and with a swab container in place in the receptacle (and the swab container cover closed). FIG. 7B shows a swab being placed into the swab container (with its cover open, to allow receipt of the swab); a sample collection vessel is also shown in position for placement into a sample collection vessel receptacle in the cartridge.

FIG. 9A shows a closed swab container; FIG. 9B shows an open swab container; FIG. 9C shows an open swab container with a swab partially inserted into the interior channel of the swab container (the interior channel is in fluid communication with the assay chamber of the swab container as shown); FIG. 9D shows the swab container with its lid partially closed, ready to sever the shaft of a swab that is in place within the interior channel; FIG. 9E shows a swab container in a closed configuration with a pipette in place in the interior channel.

DETAILED DESCRIPTION

Figure 1A:
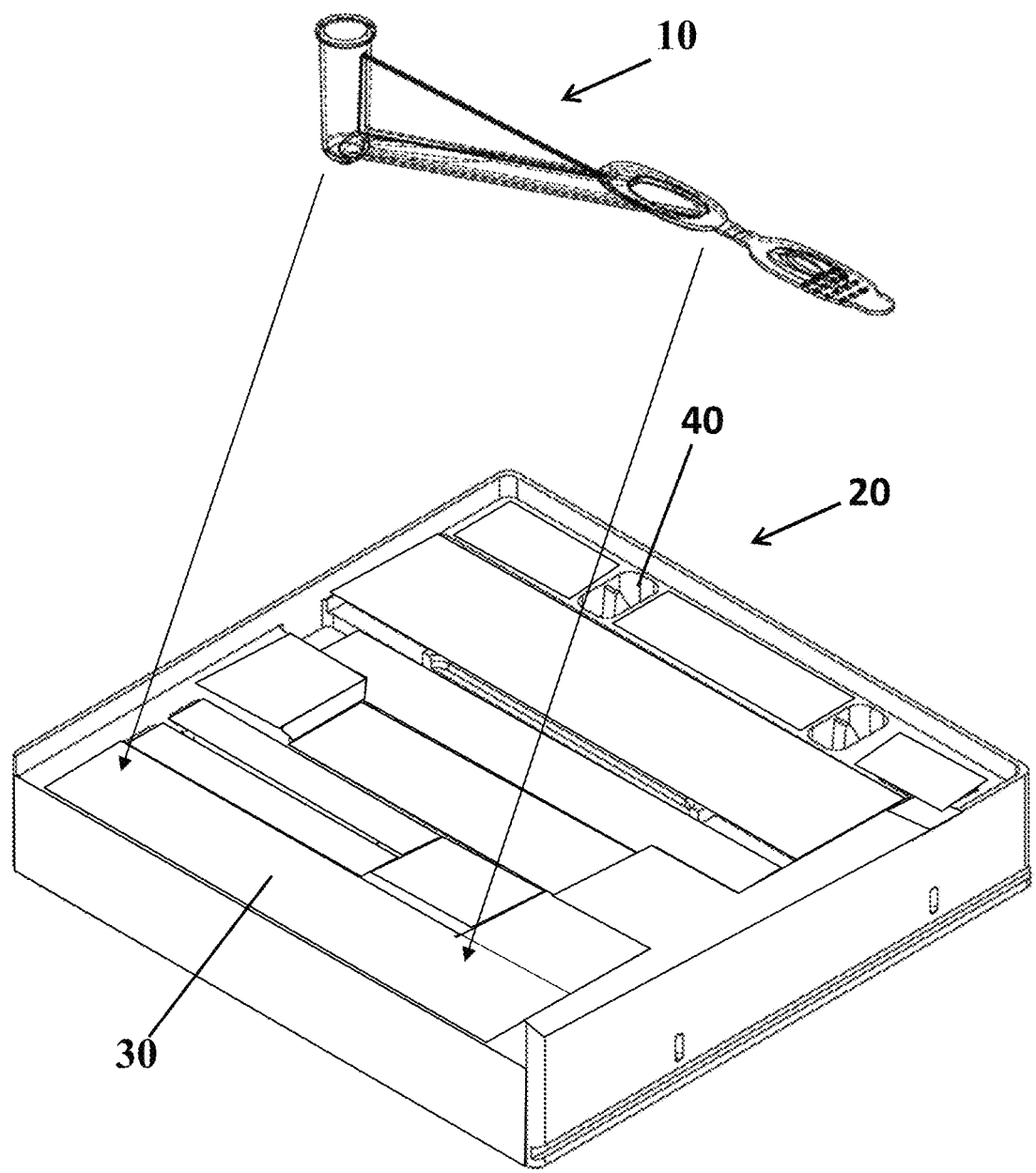
FIG. 1A shows an exemplary vessel for holding a swab (a swab container) and an exemplary cartridge which includes receptacles (cavities and wells for, e.g., a swab container, reagent vessels, assay units, mixing vessels, transport units, pipette tips, waste vessels, and sample collection vessels), and is configured to hold reagent vessels, reaction vessels, and other vessels and implements. Arrows leading away from the swab container indicate how the swab container may be placed into a receptacle in the cartridge.

Embodiments of devices, systems, and methods for sample analysis may be found, for example, in U.S. Pat. Nos. 8,088,593; 8,380,541; International Patent Application PCT/US2013/052141, filed Jul. 25, 2013; U.S. Patent Application Ser. No. 61/874,976, filed Sep. 6, 2013; U.S. Patent Application Ser. No. 61/885,462, filed Oct. 1, 2013; U.S. Patent Application Ser. No. 62/001,039, filed May 20, 2014; U.S. Patent Application Ser. No. 62/001,053, filed May 21, 2014; U.S. Patent Application Ser. No. 62/010,382, filed Jun. 10, 2014; U.S. Patent Application Ser. No. 61/885,467, filed Oct. 1, 2013; U.S. Patent Application Ser. No. 61/879, 664, filed Sep. 18, 2013; U.S. Patent Application Ser. No. 61/805,923, filed Mar. 27, 2013; U.S. Patent Application Ser. No. 61/837,167, filed Jun. 19, 2013; U.S. Patent Application Ser. No. 61/874,976, filed Sep. 6, 2013; U.S. Patent Application Ser. No. 61/766,116, filed Feb. 18, 2013; U.S. Patent Application Ser. No. 61/802,194, filed Mar. 15, 2013; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; and U.S. patent application Ser. No. 13/244,949, filed Sep. 26, 2011, the disclosures of which patents and patent applications are all hereby incorporated by reference in their entireties.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like.

It is further noted that, as used in the specification and the appended claims, "or", as used in "A or B", refers to each of A; B; and A and B; that is, use of the word "or" includes "and/or" unless the context or an explicit statement clearly dictates otherwise. Thus, for example, reference to "treatment of cells or substrate" may include treatment of cells alone; treatment of substrate alone; and treatment of both cells and substrate.

References cited herein are hereby incorporated by reference in their entirety, except to the extent that they conflict with teachings explicitly set forth in this specification.

In this specification and in the claims which follow, reference will be made to a number of terms which shall be defined to have the following meanings:

As used herein, the terms "point of service" (abbreviated "POS"), "point of service location", "point of care" (abbreviated "POC"), and "point of care location" may include locations where a subject may receive a service (e.g. testing, monitoring, treatment, diagnosis, guidance, sample collection, identification (ID) verification, medical services, non-medical services, etc.); may include locations where a subject may receive care (e.g., clinical care such as diagnostic and therapeutic care), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

As used herein, the term "reagent" refers to an element, compound, or mixture which reacts with another substance, or aids in a reaction. A reagent may participate in, or aid a reaction, by providing one or more reactants of a chemical reaction; or by providing one or more agents which accelerate, modulate, quench or otherwise affect a chemical reaction; or by aiding reactants to dissolve, or to mix, or otherwise affect the ability of reactants to contact each other, or the extent of such contact; or by providing a diluent or other agent which may act to adjust the relative or absolute amounts of reactants participating in a reaction; or may have other effects or play another role in a reaction. A reagent may be solid, liquid, or gaseous; for example a reagent may be an aqueous solution including an agent which may engage in a chemical reaction with a target which may be present in a sample.

As used herein, the term "reagent vessel" refers to a structure configured to hold a reagent, e.g., for storage until the reagent is used. For example, where a reagent is a fluid (e.g., an aqueous reagent, a solvent, or other fluid) or a solid (e.g., a lyophilized reagent), a reagent vessel may be a vial, tube, or other container which may hold a desired amount of the reagent. A reagent vessel may include a cap, lid, or other closure.

As used herein, the term "mixing vessel" refers to a structure configured to hold material for mixing, e.g., to hold two or more materials at one time (e.g., a reagent and a sample). A mixing vessel may be useful for mixing two or more materials together. A mixing vessel may include a cap, lid, or other closure.

As used herein, a "waste container" or "waste vessel" refers to a container, of any suitable shape or size, configured to receive waste material (e.g., wash buffers after use, excess reagent, or other material). Such waste material may be stored in the waste container if desired, and may be transported to a disposal location for removal, or may be removed from a waste container for transport to a disposal destination.

As used herein, a "sample collection vessel" refers to a container, or device, configured to receive and retain a sample, such as, e.g., a nasal swab sample (or fluid containing material obtained from a nasal swab that had contacted a subject), a blood sample, a urine sample, a sputum sample, or other sample. A sample collection vessel may be configured to allow transport or transfer of a sample, or aliquot thereof, to another location or vessel.

As used herein, the term "implement" refers to a tool or device used during or for sample analysis. For example, an implement may be a cuvette, such as, e.g., a cytometry cuvette. For example, an implement may be a magnet, such as a magnetic bar (useful, e.g., for attracting beads or particles for isolation and concentration of target molecules in a sample). For example, an implement may be another tool or device.

As used herein, the term "cuvette" refers to a container having at least one optically translucent or transparent side, and configured to hold a sample for optical interrogation or inspection, or both.

As used herein, the term "cytometry cuvette" refers to containers having at least one optically translucent or transparent side, and configured to hold a sample (typically containing cells) for cytometric analysis; such cytometric analysis may include, e.g., microscopy, and other optical measurements and observations, such as, for example, measurements of fluorescence, optical scattering, optical absorption, optical transmittance, polarization, or other optical measurements.

As used herein, the term "assay unit" refers to a device configured for the performance of an assay; for example, an assay unit may be configured to hold sample and reactants for the performance of a chemical reaction for assaying the sample. In some cases, an assay unit may be a tubular or conical element having openings at each of two ends, the openings being connected by a channel, and containing a reagent or reagents. In embodiments, an assay unit may be configured to allow passage of light through a wall of the assay unit, and may be translucent or transparent (e.g., may have a wall, or portion of a wall, that is translucent or transparent); such passage of light may be useful in detection of an analyte, in detection of a label or marker bound to or connected with an analyte, or in detection or measurement of a concentration or other characteristic associated with an analyte, in a sample. For example, an assay unit may be configured to receive a portion of the sample (e.g., from a sample collection vessel) and may be configured to run a chemical reaction that yields a detectable signal indicative of the presence of an analyte in the sample. For example, an assay unit may be configured to run, or to participate in, an immunoassay. For example, an assay unit may be configured to run, or to participate in, a nucleic acid assay. For example, an assay unit may be configured to run, or to participate in, a general chemistry assay. For example, an assay unit may be configured to run, or to participate in, a cytometric assay.

As used herein, the term "pipette tip" refers to a tubular device having openings at each of two ends, the openings being connected by a channel; pipette tips may be cylindrical or have other shapes; for example, pipette tips are often tapered, and thus may have a conical shape. Pipette tips are useful for aspiration of fluids, and may be used to collect, transport, mix, or otherwise contact a fluid or fluids. In some embodiments, a wider end may be configured to engage a grasping or aspiration mechanism, providing mechanical support, transport, and/or fluid flow (e.g., suction or ejection) at or via the wider end. In some embodiments, a narrower end may be configured to contact a fluid, and may be configured for aspiration of fluid into the pipette tip via the narrower end. A pipette tip may include a filter or baffle within the channel so as to prevent contamination (e.g., either of a grasping or aspiration mechanism at one end of the pipette tip, or of fluid within or to be contacted by the pipette tip, or both). A pipette tip may be useful, for example, for aspiration of sample or other fluid, for mixing, for transport, or other uses.

As used herein, a "touch-off pad" refers to a location configured to drain or wipe excess fluid (e.g., reagent, diluent, sample, or other fluid) from a pipette tip. A touch-off pad typically includes an absorbent material for contacting a pipette tip, and is configured to wick or absorb liquid from the pipette tip upon contact between the pipette tip and the touch-off pad. A touch-off pad may be soft or resilient as well as absorbent. A touch-off pad may be made with, for example, paper (e.g., an absorbent paper such as a filter paper); fiber (e.g., either natural or artificial fiber woven or matted together); plastic; or other material.

As used herein, a "transport mechanism" refers to a device or system which may engage an object and move the object from one place to another. Sample handling systems (including fluid handling systems) may be, or include, a transport mechanism. A pipette having a nozzle may be used, for example, to engage a pipette tip (e.g., by pressure fit of the nozzle within a wider end of the pipette tip) effect to hold the pipette tip and to move the pipette tip from a first location to a second location. The pipette tip may be released from the nozzle at the second location (e.g., by movement of a ring or bar configured to push the pipette tip off of the nozzle).

As used herein, the term "transport unit" refers to a tool that is configured to hold one or more other objects for transport; for example, a transport unit may have a frame with holes or receptacles configured to retain one or more of a pipette tip, or an assay unit, or a mixing vessel, or a cuvette, or a waste vessel, or a sample collection vessel, or combinations of these. A transport unit may be configured to hold other objects for transport. A transport unit may be configured to interface with, and to be carried by, a transport mechanism (such as, e.g., a sample handling system or fluid handling system) which may include a means for grasping a transport unit, a means for transporting a transport unit to a desired location, and a means for depositing a transport unit at the desired location. Transport of a transport unit, where the transport unit retains one or more tips or vessels, or other implements, is effective to move such tips or vessels, or other implements, to a desired location. For example a transport unit may be configured to engage with a nozzle of a transport mechanism, e.g., in a way similar to that described for engagement of a pipette tip with a nozzle of a sample handling system.

As used herein, the term "sample" refers to a fluid, tissue, secretion, excretion, or other material collected from a subject. Examples of biological samples include but are not limited to, blood, serum, plasma, bone marrow, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk and/or other secretions or excretions. Biological samples may include nasopharyngeal wash, or other fluid obtained by washing a body cavity or surface of a subject, or by washing a swab following application of the swab to a body cavity or surface of a subject.

Nasal swabs, throat swabs, stool samples, hair, finger nail, ear wax, breath, and other solid, semi-solid, or gaseous samples may be processed in an extraction buffer, e.g., for a fixed or variable amount of time, prior to their analysis. The extraction buffer or an aliquot thereof may then be processed similarly to other fluid samples if desired. Examples of tissue samples of the subject may include but are not limited to, connective tissue, muscle tissue, nervous tissue, epithelial tissue, cartilage, cancerous sample, or bone. The sample may be obtained from a human or animal. The sample may be obtained from a vertebrate, e.g., a bird, fish, or mammal, such as a rat, a mouse, a pig, an ape, another primate (including humans), a farm animal, a sport animal, or a pet. The sample may be obtained from a living or dead subject. The sample may be obtained fresh from a subject or may have undergone some form of pre-processing, storage, or transport.

A sample may be of any suitable size or volume, and is preferably of small size or volume. In some embodiments of the assays and methods disclosed herein, a sample may comprise a small volume sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1

μL; or comprises no more than about 0.8 μL; or comprises no more than about 0.5 μL; or comprises no more than about 0.3 μL; or comprises no more than about 0.2 μL; or comprises no more than about 0.1 μL; or comprises no more than about 0.05 μL; or comprises no more than about 0.01 μL.

Samples and Sample Analysis

Samples from the throat of a subject may be obtained, e.g., by a throat swab; samples obtained from the nose of a subject may be obtained, e.g., by a nasal swab. In embodiments, samples obtained from the throat and from the nose of a subject may be tested together. In embodiments, testing of samples obtained from the throat, or from the nose, or from both the nose and from the throat, may be tested by nucleic acid analysis; or by amino acid analysis (e.g., ELISA or other antibody-based or binding protein-based analysis); or by general chemistry analysis; or by cytometric analysis; or by combinations thereof. For example, samples may be tested by nucleic acid analysis and by amino acid analysis. Such tests may be used to determine how long a subject has had an infection, for example, by noting the delay in rise of levels of antibodies indicative of a particular disease in the sample; or by tracking the rise in the levels of antibodies indicative of a particular disease in the sample over time (e.g., by repeated testing over time). Similarly, such testing may be used to detect, or to determine, the effect of treatment, by noting the delay in rise of levels of antibodies indicative of a particular disease in the sample; or by tracking the rise in the levels of antibodies indicative of a particular disease in the sample over time (e.g., by repeated testing over time). In embodiments, samples from throat and from nose may be included in a single solution, and tested together. In embodiments, samples from throat and from nose may be in separate vessels (e.g., sample containers), but both included in a single cartridge, and the separate vessels tested at the same time. Such testing at the same time may comprise testing the vessels separately, or may include mixing the contents of the vessels and testing the mixture.

In embodiments, Applicants provide systems, methods, and devices for detecting a plurality of disease-causing agents in a single clinical sample, or in a plurality of aliquots of a single clinical sample. In embodiments, a single clinical sample may be a small volume clinical sample of blood, sputum, tears, nasal swabs, throat swabs, cheek swabs, or other bodily fluid, tissue, secretion, or excretion taken from a subject. In embodiments, a single clinical sample has a volume of less than about 500 μL, or less than about 250 μL, or less than 150 μL, or less than about 100 μL, or less than about 50 μL, or less than about 25 μL, or less than about 10 μL, or less than about 5 μL, or less than about 1 μL, or less.

In embodiments, clinical samples may be obtained at a point-of-service (POS) location. A POS location may be, for example, a retail pharmacy, a supermarket, a hospital, a clinic, a physician's office, or other location. Clinical samples may be tested at the POS location for multiple markers indicative of agents which may cause one or more of a plurality of diseases (e.g., at least 8, or at least 10, or at least 12, or at least 20, or at least 30, or at least 40, or at least 50, or at least 60, or more markers, indicative of the same or similar numbers of different diseases). The testing may be completed in a short period of time. In embodiments, the short period of time may be measured from the time the sample is inserted into a device or system for performing an analysis. In embodiments, the short period of time may be measured from the time the sample is obtained from the subject.

In embodiments, clinical samples may be analyzed at a POS location. In embodiments, clinical samples obtained at a POS location may be analyzed at the same POS location. In embodiments, clinical samples may be obtained at a point-of-service (POS) location and may be analyzed at a different location. In embodiments, clinical samples may be analyzed in a short period of time, e.g., in a period of time that is less than about 5 hours, or less than about 4 hours, or less than about 3 hours, or less than about 2 hours, or less than about 1 hour, or less than about half an hour.

Swab Containers

Figure 1B:
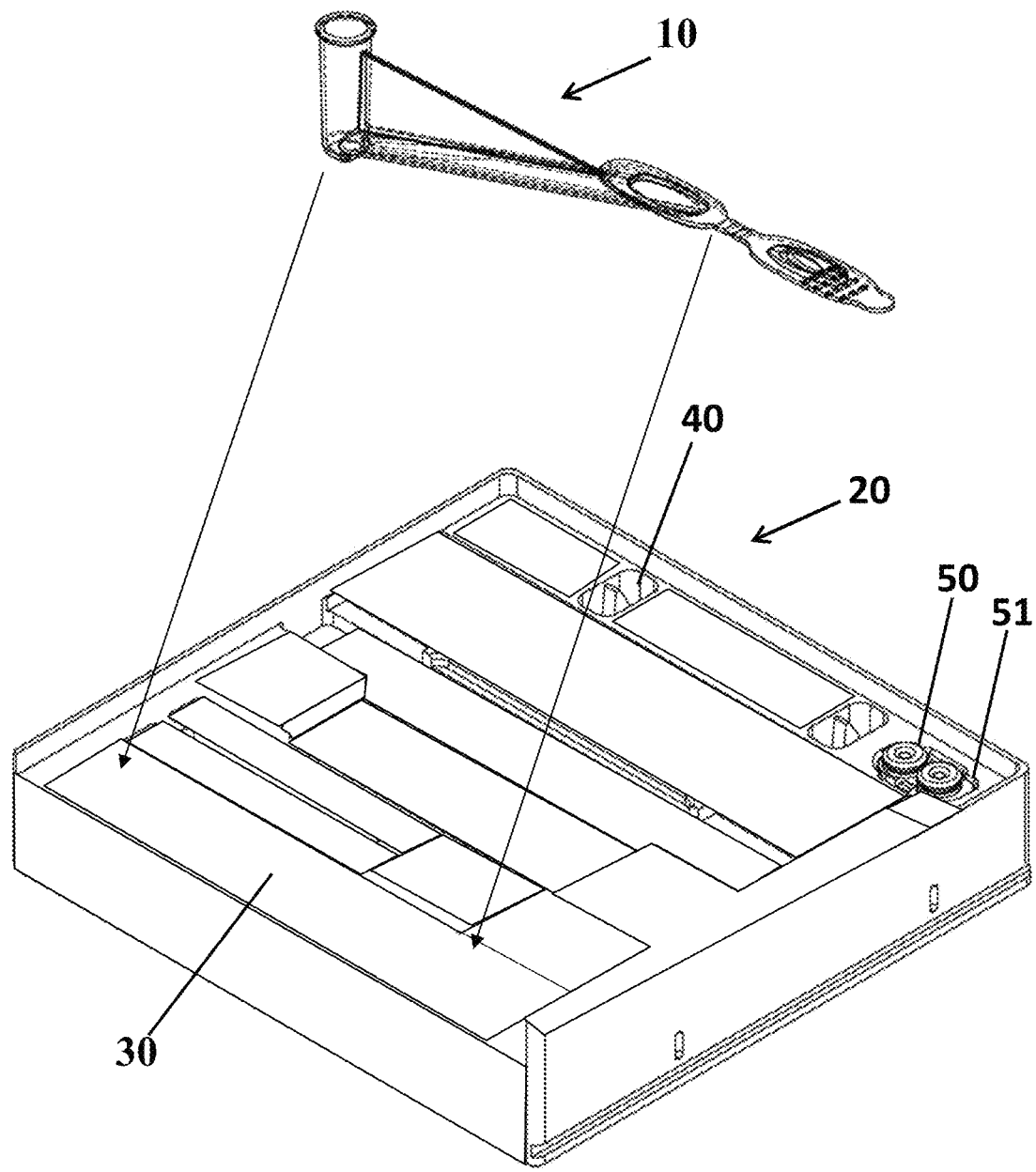
FIG. 1B shows an exemplary swab container (configured for holding a swab) and an exemplary cartridge (which includes cavities and wells for reagents and vessels, and is configured to hold reagent vessels, reaction vessels, and other vessels and implements). In addition to the cavities and wells configured to hold reagent vessels, reaction vessels, and other vessels and implements as shown in the embodiment of FIG. 1A, the exemplary cartridge shown in FIG. 1B includes cavities and wells suitable for holding other sample vessels, e.g., blood or urine sample vessels, in addition to swab containers. Arrows leading away from the swab container indicate how the swab container may be placed into a receptacle in the cartridge.
Figure 1C:
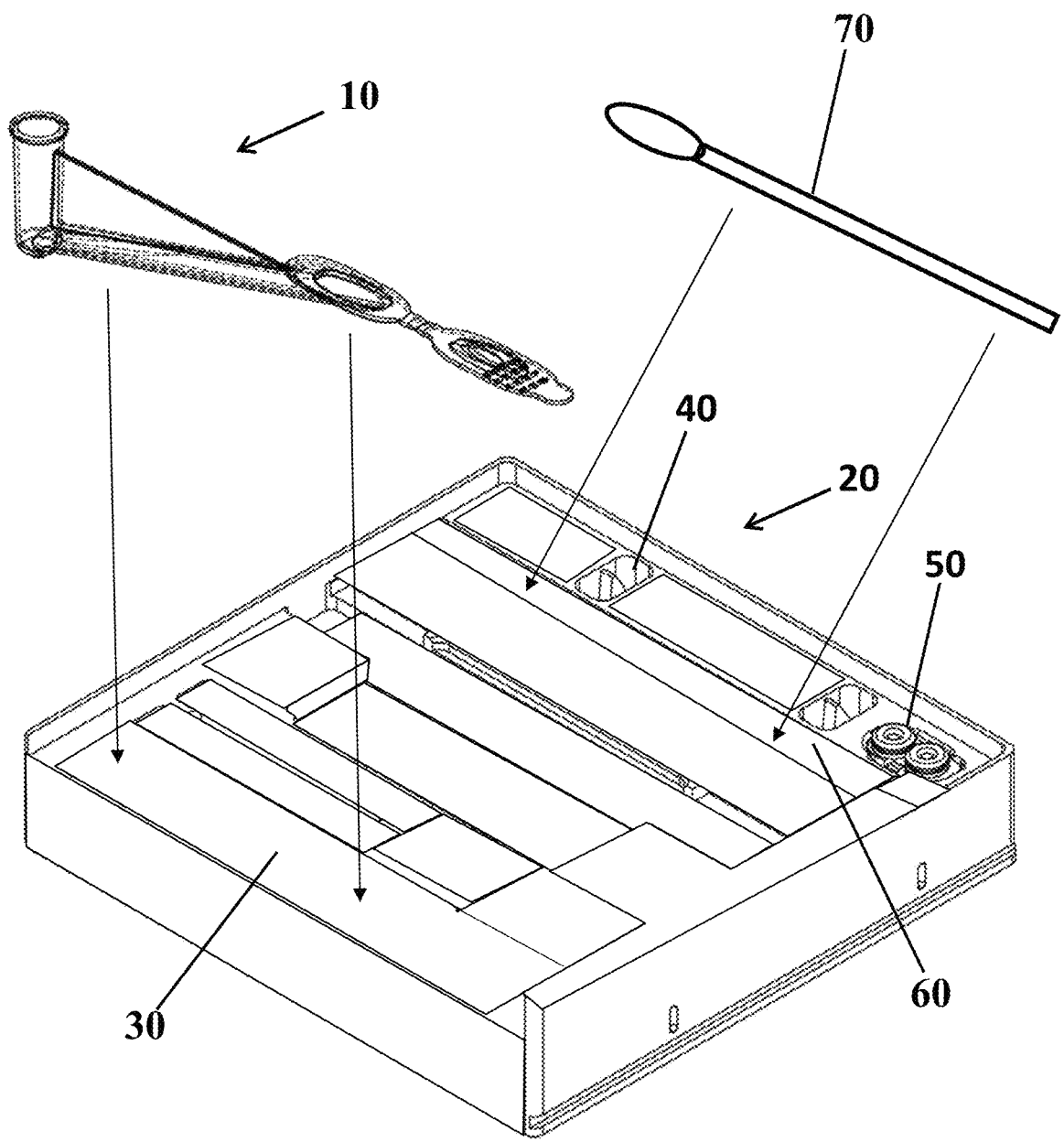
FIG. 1C shows an exemplary swab container, and an exemplary cartridge which includes cavities and wells for holding a swab and a swab container, as well as cavities and wells configured to hold reagent vessels, reaction vessels, and other vessels and implements (which may optionally include other sample vessels, e.g., blood or urine sample vessels). Arrows leading away from the swab indicate how the swab may be placed into a swab receptacle in the cartridge. Arrows leading away from the swab container indicate how the swab container may be placed into a swab container receptacle in the cartridge.

As shown in FIG. 1A, FIG. 1B, and FIG. 1C, a vessel for holding a swab may be loaded onto a cartridge, where it may be retained until needed for analysis; the cartridge may be loaded onto an analysis device or analysis system, thereby loading the swab (and any other samples or sample containers on the cartridge as well). FIGS. 1A, 1B, and 1C show exemplary containers for holding a swab (a swab container) and exemplary cartridges (which includes cavities and wells for reagents and vessels, and is configured to hold one or more of reagent vessels, assay units, mixing vessels, pipette tips, transport units, and other vessels and implements, including other sample vessels, e.g., blood or urine sample vessels). Arrows leading away from the swab container indicate how the swab container may be placed into a receptacle in the cartridge.

As shown in FIG. 1A, a vessel for holding a swab (a swab container 10) may be loaded onto a cartridge 20 by placement into a receptacle 30. The cartridge 20 as shown also includes cavities and wells 40 for receiving and holding reagents and vessels. A swab container 10 may contain a swab in place within the swab container 10, or may be loaded onto a cartridge without a swab in place within the swab container 10.

As shown in FIG. 1B, a swab container 10 may be loaded onto a cartridge 20 by placement into a receptacle 30. The cartridge 20 as shown also includes cavities and wells 40 for receiving and holding reagents and vessels. In the embodiment shown in FIG. 1B, the cartridge 20 also includes a sample collection vessel 50, which may hold, e.g., blood, urine, or other sample. The arrows leading away from the swab container 10 indicate how the swab container 10 may be placed into a receptacle 30 in the cartridge 20. Thus, as shown in FIG. 1B, a swab container 10 may be loaded onto a cartridge 20, where it may be retained until needed for analysis; the cartridge 20 may be loaded onto an analysis device or analysis system, thereby loading the swab container 10 (and any sample container or sample containers that are also in place on the cartridge 20 as well). A cartridge 20 may have a receptacle 30. As shown in FIG. 1B, a swab container 10 may be loaded onto a cartridge 20 by placement into a receptacle 30. The cartridge 20 as shown also includes cavities and wells 40 for receiving and holding reagents and vessels. The cartridge 20 as shown also includes a sample collection vessel 50, which may hold, e.g., blood, urine, sputum, or other sample. The sample collection vessel 50 is shown in position in a sample collection vessel receptacle 51 in the cartridge 20. The arrows leading away from the swab container 10 indicate how the swab container 10 may be placed into a receptacle 30 in the cartridge 20.

As shown in FIG. 1C, a swab container 10 may be loaded onto a cartridge 20 by placement into a receptacle 30. The cartridge 20 as shown also includes cavities and wells 40 for receiving and holding reagents and vessels. As shown in the embodiment of FIG. 1C, the cartridge 20 includes a swab receptacle 60 configured to hold a swab 70. In embodiments (e.g., in the embodiment illustrated in FIG. 1C) a cartridge 20 having a swab receptacle 60 may optionally include a sample collection vessel 50, which may hold, e.g., blood, urine, or other sample. Such a swab 70 may be held in swab receptacle 60 prior to its use in collecting a sample. In embodiments, a swab 70 may be placed within a swab container 10 after collection of a sample with swab 70. In the embodiment shown in FIG. 20C, swab container 10 may be loaded onto a cartridge without a swab in place within the swab container 10 prior to use of swab 70, and swab container 10 may be replaced in a receptacle 30, holding swab 70 within swab container 10 after collection of a sample by swab 70.

A swab container as disclosed herein may be made with any suitable material. For example, a swab container may comprise a material selected from glass, plastic, polymer, rubber, metal, composite, or other material, or combination of materials. In embodiments, a swab container may be made from, e.g., polypropylene, polycarbonate, polystyrene, polyurethane, polyethylene, polyacrylamide, polyacrylate, polymethacrylate, polymethylmethacrylate (PMMA), poly (4-methylbutene), other acrylic, polydimethysiloxanes (PDMS), polyvinylchloride (PVC), poly(vinyl butyrate) polysulfone, acrylonitrile-butadiene-styrene (ABS), poly (ethylene terephthalate), a fluorocarbon polymer (e.g., polytetrafluoroethylene (PTFE or Teflon®)), nylon, a co-polymer, or combinations thereof. A swab container as disclosed herein may be molded, blown, machined, assembled from parts, made using 3-D printing techniques, or by other methods, or by any combination of methods.

FIGS. 2A-2E show views of an exemplary swab container 10 having a cover 12 flexibly attached to the conduit 14 near to the entry port 16. These figures also show an assay chamber 13 having an assay port 17, and a rib 15 of a swab container 10 which provides structural support to the swab container 10. FIG. 2A shows a side view, and FIG. 2B shows a top perspective view, while FIG. 2C provides an exploded view of a portion of the cover 12 (circled at "C" in FIG. 2A) showing a lip 18 which is configured to secure the cover 12 when the cover 12 is placed within the entry port 16 during closure of the entry port 16. Cover 12 may be closed over entry port 16 with all or a portion of a swab handle disposed within the interior channel 22 of a conduit 14; a handle may be broken if necessary to shorten the handle portion and to allow closure of the entry port 16. In embodiments, a cover 12 may fit entirely within an entry port 16; in other embodiments, a cover 12 may contact, and may at least partially cover, a rim 21 of an entry port 16. FIG. 2D provides an exploded view of the region circled at "D" in FIG. 2A, showing the linkage between a region near the entry port 16 and cover 12. The thinning of the neck portion shown in the expanded view shown in FIG. 2D facilitates flexing and bending of the linkage, and so aids in closure of the cover 12 over entry port 16. In the embodiment shown in FIGS. 2A-2E, lip portion 18 fits within entry port 16, while tab 19 (which may be useful for manual manipulation of cover 12) may at least partially cover rim 21 when cover 12 is in place covering entry port 16. Cover 12 may be closed over entry port 16 with all or a portion of a swab handle disposed within the conduit; a handle may be broken if necessary to shorten the handle portion and to allow closure of the entry port 16.

It will be understood that a cover 12 may be attached to a swab container 10 by any suitable means, or may be a separate part that may be placed on or into an entry port 16. In embodiments, a cover 12 may be a rubber cover, or plug. In embodiments, a cover 12 may be an aluminized plastic sheet, or aluminum foil, or other cover glued, crimped, or otherwise disposed over an entry port 16.

An assay port 17 of a swab container 10 may be covered with a cover (not shown). For example, such a cover for an assay port 17 may be a pierceable cover (e.g., aluminum foil, or an aluminized plastic sheet, which may be attached by adhesive, crimped, or attached by other means to the assay chamber 16 or otherwise attached so as to extend over and cover assay port 17). In embodiments, such a cover for an assay port 17 may be a detachable cover (e.g., a rubber or plastic stopper or cap). In embodiments, a cover for an assay port 17 may be attached to a swab container 10 (e.g., may be attached to assay chamber 16).

A swab container as disclosed herein may be of any suitable size. A swab container 10 as shown, for example, in FIGS. 2A and 2B may have dimensions whereby the distance between an assay port 17 and an entry port 16 may be between about 25 millimeters (mm) and about 250 mm; or may be between about 50 mm and about 200 mm; or may be between about 75 mm and about 150 mm; or may be between about 80 mm and about 120 mm; or other distance. In embodiments, an assay chamber 13 may have a height of between about 10 mm and about 100 mm; or may have a height of between about 15 mm and about 75 mm; or may have a height of between about 20 mm and about 60 mm; or may have a height of between about 25 mm and about 50 mm; or other height. As shown in FIGS. 2A and 2B, an assay port 17 may have a circular shape. In embodiments, an assay port 17 having a circular shape may have a diameter, where the size of such a diameter may be, for example, between about 0.5 mm to about 25 mm; or between about 1 mm and about 20 mm; or between about 2 mm and about 15 mm; or between about 3 mm and about 10 mm; or other diameter. It will be understood, however, that an assay port 17 may have any suitable shape (e.g. circular, oval, square, rounded square, rectangular, rounded rectangular, triangular, rounded triangular, or other shape). The dimensions of assay ports of such other shapes (e.g., a side of a square, or rectangle, or triangle; or a long or short axis of an oval) will typically be found within similar ranges as the diameter ranges disclosed herein. As shown in FIGS. 2A and 2B, an entry port 16 may have an oval, or rounded rectangular, shape. It will be understood that an entry port 16 may have any suitable shape (e.g. circular, oval, square, rectangular, triangular, or other shape). In embodiments, an entry port 16 may have a dimension, such as a long axis, of between about 0.5 mm to about 25 mm; or between about 1 mm and about 20 mm; or between about 2 mm and about 15 mm; or between about 3 mm and about 10 mm; or other dimension.

An alternative embodiment of a swab container 10 is shown in FIG. 2E. A swab container 10' as illustrated in FIG. 2E may be assembled for use from two parts, a forward portion (labeled "F") and a rear portion (labeled "R") which fit snugly together at mating point M. When assembled, a conduit 14 extends from entry port 16 to assay chamber 13. A swab container 10' as shown in FIG. 2E may be disassembled (e.g., after insertion of a swab) into a forward portion F and a rear portion R; the forward portion R may be suitable for placement in a cartridge such as a cartridge 20 as illustrated in FIG. 1.

Figure 3A:
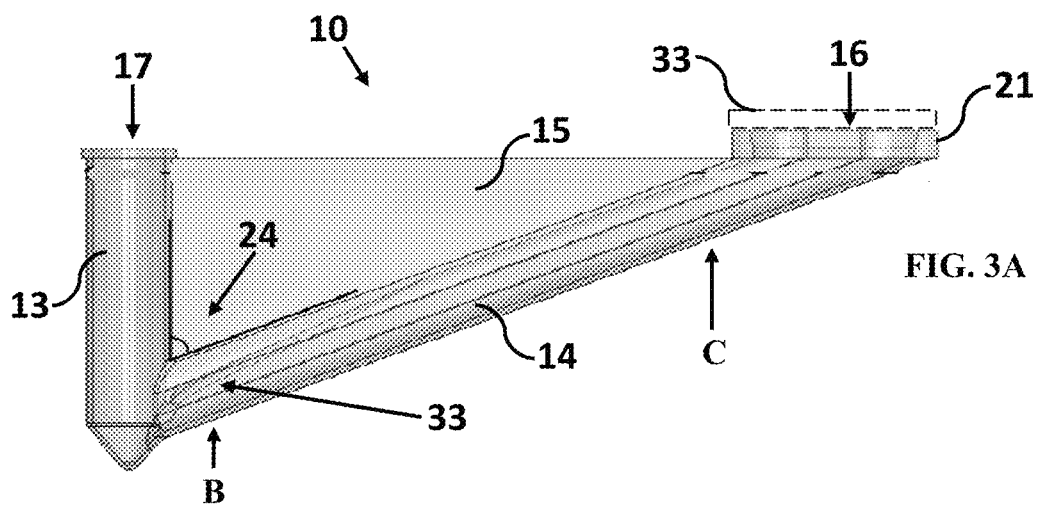
FIGS. 3A-3C show a side view of a swab container 10 lacking an attached cover.
Figure 3B:
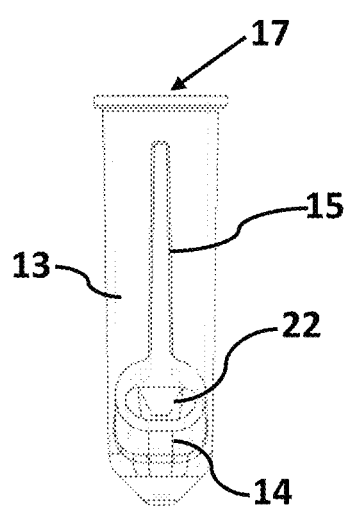
Figure 3C:
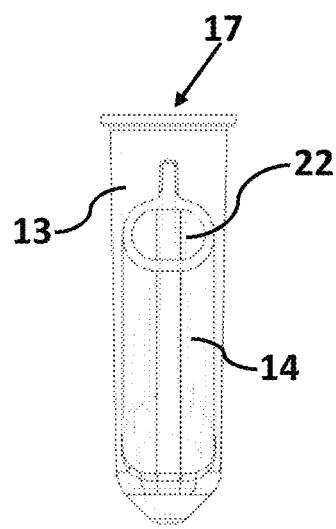

FIGS. 3A-3C show a side view of a swab container 10 having an entry port 16; in this embodiment, the entry port 16 lacks an attached cover. In embodiments, a detachable cover 33 may be placed in or on the entry port 16. In embodiments, such a detachable cover 33 may include a rubber stopper, or plastic lid, or may be a pierceable cover (e.g., aluminum foil, or an aluminized plastic sheet, which may be crimped, or attached by adhesive or by other means to rim 21 of entry port 16). In embodiments, a cover 33 may be a porous cover, such as, e.g., filter paper, or gauze, or mesh, or other porous or semi-porous cover placed so as to cover the entry port 15). It will be understood that a swab container 10 as illustrated in FIGS. 3A-3C may also have a cover over assay port 17 (not shown). FIG. 3A provides a side view, and FIGS. 3B and 3C provide cross-sectional views showing the interior channel 22 within the conduit 14 of the swab container 10. A portion of an interior channel 22 may have a narrowing, as indicated by arrow 33 in FIG. 3A, and as shown in the cross-sections of FIGS. 3B and 3C. FIG. 3B provides a cross-section taken along a line as indicated by the arrow labeled "B" in FIG. 3A, showing the narrowing of the interior channel 22 near the assay chamber 13. FIG. 3C provides a cross-section taken along a line as indicated by the arrow labeled "C" in FIG. 3A, showing the interior channel 22 near the entry port 16; the interior channel 22 is narrower near the assay chamber 13 (see FIG. 3B) than it is near the entry port 16 (see FIG. 3C); such narrowing (e.g., as indicated by arrow 33) is configured to squeeze a swab (e.g., a swab tip) pushed through or in place in the interior channel 22, effective to aid in the release of sample material carried by the swab. In embodiments, such a narrowing may be configured to prevent the entry of a swab (e.g., a swab tip) into an assay chamber 13. Such a narrowing of an interior channel 22 may be accomplished by, e.g., a symmetric narrowing of the channel; an asymmetric narrowing of the channel; by inclusion of a feature (e.g., a protrusion such as a bump, a wedge, a knob, a baffle, rib, or other feature) in a wall of the interior channel, wherein the feature may be oriented longitudinally along the channel wall, laterally along the wall, or at some other orientation relative to a longitudinal axis of the channel; by a bend in the channel; or by other means, or by a combination of means. In some embodiments, the interior channel 22 narrows to a size wherein the swab does not enter the assay chamber 13 when the swab is fully inserted. Such an embodiment may have fluid communication between the channel and the assay chamber 13 but the swab does not physically enter the assay chamber 13. Optionally, some embodiments may allow for at least a portion of the swab to enter the assay chamber 13.

FIG. 3A also shows contact angle 24 between conduit 14 and assay chamber 13. A contact angle 24 may be any suitable angle. In embodiments, a contact angle 24 may be between about 10° to about 90°. In embodiments, a contact angle 24 may be between about 40° to about 85°. In embodiments, a contact angle 24 may be between about 70° to about 80°. In the embodiment shown in FIG. 3A, the contact angle is about 75°.

Figure 4A:
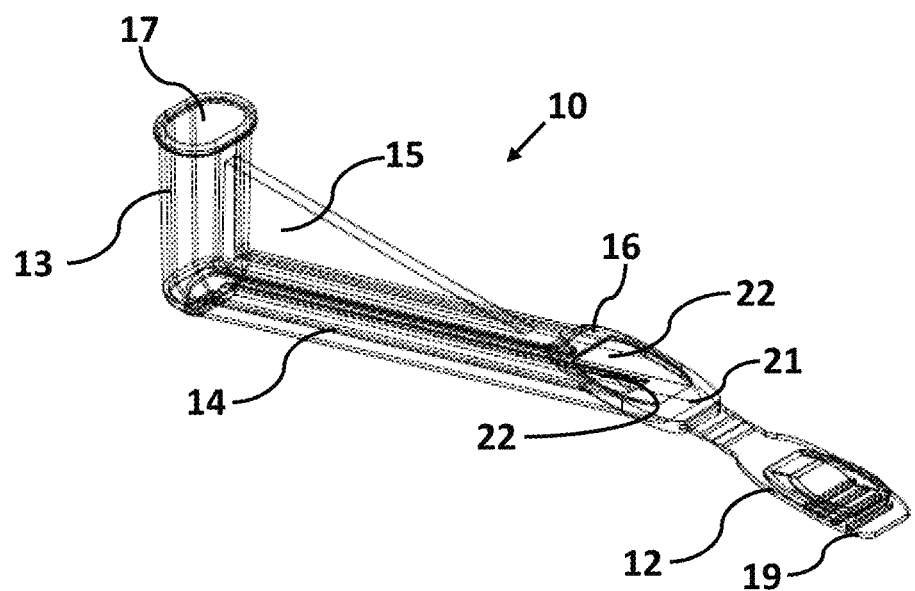
FIGS. 4A-4B provide a top perspective view (FIG. 4A) and a cross-sectional view (FIG. 4B) showing a swab container having a conduit which has two interior channels, both of which connect to the assay chamber and to the entry port.
Figure 4B:
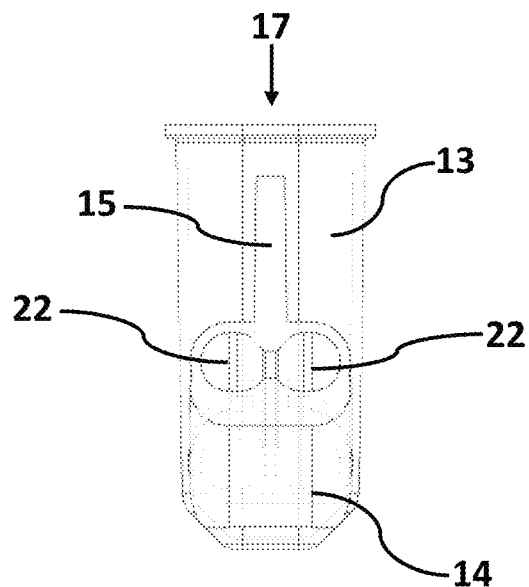

FIGS. 4A-4B provide a top perspective view (FIG. 4A) and a cross-sectional view (FIG. 4B) showing one embodiment of a swab container 10 having a conduit 14 having two interior channels 22 connecting entry port 16 with assay chamber 13. As shown, cover 12 in FIG. 4A may be used to close off entry port 16, sealing both interior channels 22. In embodiments, a cover 12 may be configured to close only a single interior channel 22, e.g., to allow closure of a first interior channel 22 after placement of a first swab therein, while allowing continued access for placement of a second swab in a second interior channel 22. For example, in embodiments, a cover 12 may be configured to close only a single interior channel 22 at a time (e.g., may be split into two portions which may close independently of each other, allowing closure of a first interior channel 22 after placement of a first swab therein, while allowing continued access to second interior channel 22; the second portion of such a cover 12 may be closed following placement of a second swab in a second interior channel 22 or at any other desired time). In embodiments, a swab container 12 may include two covers 12 which may be positioned independently of each other.

It will be understood that, in further embodiments, a swab container may hold two swabs in a single interior channel; or a swab container may hold three or more swabs in a single interior channel. The orientation of the swabs in the same channel may be top-bottom, side-by-side, diagonally oriented, or other configuration depending in part on channel cross-sectional shape. As shown in the examples of FIGS. 4A and 4B, a swab container configured to hold two swabs may have conduits (and interior channels) that are substantially parallel to each other (e.g., the long axes of the conduits (and interior channels) form an angle with respect to each other of less than about 5°). In further embodiments, a swab container configured to hold two, to hold more than two, swabs, may have conduits (with interior channels) which are not substantially parallel, but are placed at angles to one another. For example, a pair of conduits (of a swab container having two, or three, or more conduits) may be substantially perpendicular to one another (e.g., may have long axes that form an angle close to 90°, that is, between about 85° and about 95°), or may form an angle of about 45°; or may form an angle of between about 5° to about 175°; or may form any other angle. In embodiments, a swab container configured to hold two, or configured to hold more than two, swabs, may have conduits (with interior channels) with long axes which are substantially in line with each other on opposite sides of an assay chamber (e.g, the long axes form an angle of between about 175° to about 185°). In embodiments, such swab containers having two, three, or more conduits may have interior channels each of which connect with the same assay chamber. In embodiments, such swab containers having two, three, or more conduits may have interior channels which connect with the different assay chambers.

It will be understood that placement of a swab into a swab container 10 allows transfer of sample material into a reagent, e.g., a fluid, for transport to another location or to a sample analysis device, or for analysis in the assay chamber 13 itself. An assay chamber 13 may be filled (to any desired degree, e.g., either partially or completely) with a reagent for bathing a swab (i.e., for bathing at least a tip of a swab); an interior channel 22 may be filled (to any desired degree, e.g., either partially or completely) with a reagent for bathing a swab; such a reagent may be or include, for example, a transport medium (such as, e.g., Copan Universal Transport Medium® (UTM-RT) (Copan Diagnostics Inc., Murrieta, CA, USA) or other transport medium), saline, distilled water, or other reagent suitable for bathing a swab. A reagent for bathing a swab may aid in releasing sample material from the swab for analysis. Such release of sample into a reagent provides fluid containing sample material which may be used for sample analysis. The reagent containing sample material may then be used to transport the fluid to a location or device for analysis, or the swab container itself may be used, at least in part, for analysis of the fluid. It should be understood that although the term assay chamber is used herein, at least some embodiments are configured to perform only sample preparation in the chamber and that the assay itself will be performed elsewhere. In this non-limiting example, sample is prepared in the assay chamber and at least one portion of the prepared sample is extracted from the assay chamber for performing assay(s) at another location. It should also be understood that if a fluid is used in the assay chamber 13, the fluid level may be selected so that at least a portion of the handle of the swab is also bathed in the fluid when the swab is fully inserted. In this non-limiting example, sample on the handle can also be drawn into the fluid and increase the amount of sample in the fluid, which can be helpful when the amount of sample collected is small. In one embodiment, at least 10% of the length of the handle is covered by the fluid when the swab is fully inserted. Optionally, at least 20% of the length of the handle is covered by the fluid when the swab is fully inserted. Optionally, at least 30% of the length of the handle is covered by the fluid when the swab is fully inserted. Optionally, at least 40% of the length of the handle is covered by the fluid when the swab is fully inserted. Optionally, at least 50% of the length of the handle is covered by the fluid when the swab is fully inserted. Optionally, at least 60% of the length of the handle is covered by the fluid when the swab is fully inserted. Optionally, at least 70% of the length of the handle is covered by the fluid when the swab is fully inserted. Optionally, at least 80% of the length of the handle is covered by the fluid when the swab is fully inserted. Optionally, at least 90% of the length of the handle is covered by the fluid when the swab is fully inserted. Optionally, at least 95% of the length of the handle is covered by the fluid when the swab is fully inserted.

Thus, for example, an assay chamber 13, interior channel 22, or both, may contain water; or an assay chamber 13, interior channel 22, or both, may contain a water solution including salts, or buffers, or surfactants, or solvents, or emulsifiers, or other elements. An assay chamber 13, interior channel 22, or both, may contain a reagent for bathing a swab, such a reagent including a salt, or combination of salts, such as physiological salts (e.g., Hank's Balanced salts, or other salt combination providing salt concentrations near to normal mammalian physiological salt concentrations). In embodiments, the salt concentration of a reagent for bathing a swab may be a low concentration as compared to normal mammalian physiological salt concentrations. In embodiments, the salt concentration of a reagent for bathing a swab may be a high concentration as compared to normal mammalian physiological salt concentrations. A reagent for bathing a swab may include serum albumin or other serum product, such as, e.g., bovine serum albumin, fetal calf serum, horse serum, or the like. A reagent for bathing a swab may include gelatin. A reagent for bathing a swab may include sucrose, or glucose, or other sugar, saccharide, or oligosaccharide. A reagent for bathing a swab may include an antibiotic, such as, e.g., amphotericin, valnomycin, vancomycin, colistin, streptomycin, gentamycin, iodine, or other antimicrobial agent. A reagent for bathing a swab may include a preservative (e.g., benzoic acid, benzyl alcohol, phenol alcohol, butyl alcohol, an alkyl paraben such as methyl or propyl paraben, an ammonium chloride compound, m-cresol, resorcinol, catechol, cyclohexanol, sodium azide, chemical derivatives thereof, or other preservative). A reagent for bathing a swab may include amino acids such as, e.g., cysteine, glutamic acid, glutamate, or other amino acid. A reagent for bathing a swab may include a buffer, such as, e.g., a phosphate, citrate, ammonium, acetate, or carbonate buffer; tris(hydroxymethyl)aminomethane (TRIS); 3-(N-morpholino) propanestilibilic acid (MOPS); 3-morpholino-2-hydroxypropanesulfonic acid (MOPSO); 2-(N-morpholino)ethanesulfonic acid (MES); N-(2-Acetamido)-iminodiacetic acid (ADA); piperazine-N,N'-bis(2-ethanesulfonic acid) (PIPES); 4-(2-hydroxyethyl)-1-piperazine ethanesulfonic acid (HEPES); or other buffer. For example, a reagent for bathing a swab may include a buffered aqueous solution (e.g., a saline solution) having a pH of between about pH 4 to about pH 10; or between about pH 5 to about pH 9; or between about pH 6 to about pH 8; or between about pH 6.7 to about pH 7.7; or other pH. A reagent for bathing a swab may include a pH indicator (e.g., phenol red, or other indicator). In embodiments, a reagent for bathing a swab may be, or may include a non-aqueous medium (e.g., may be or include ethanol, or dimethylsulfoxide, or other compound).

Accordingly, Applicants disclose swab containers including a reagent for bathing a swab. Such swab containers may have features as disclosed herein, including, but not limited to, any or all features of swab containers 10 as illustrated in any of the figures provided herein. In embodiments, a reagent for bathing a swab may be contained within at least a portion of an assay chamber of a swab container. In embodiments, a reagent for bathing a swab may be contained within at least a portion of an interior channel of a swab container. In embodiments, a reagent for bathing a swab may be contained within at least a portion, or portions, of both an assay chamber and an interior channel of a swab container.

Figures 5A, 5B:
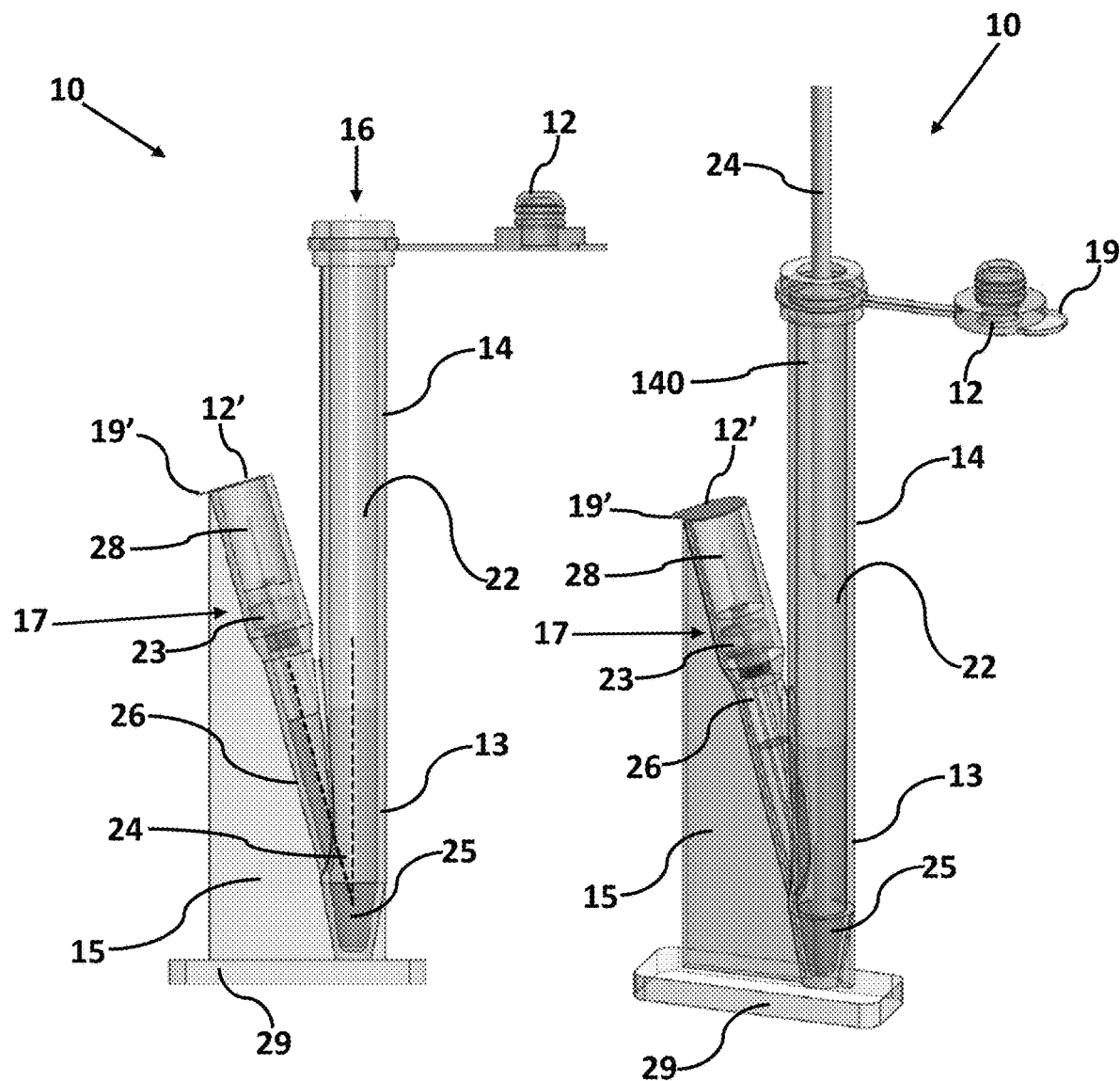
FIGS. 5A-5B provide an example of a swab container configured to receive a swab; the swab container is shown without a swab in FIG. 5A, and shown with a swab in place in FIG. 5B. A cover is shown attached to the conduit near the entry port which may be used to close the entry port.

FIGS. 5A-5B an example of a swab container configured to receive a swab (the container is shown without a swab in FIG. 5A, while a swab 24 is shown in place in the assay chamber 13 in FIG. 5B. The swab shown in FIG. 5B has a break-point 140 within conduit 14 and below the level of the entry port 16. In the embodiments shown in FIG. 5, the entry port 16 provides a swab 24 with access to an assay chamber 13 via a conduit 14 having an interior channel 22 within conduit 14. A cover 12 flexibly attached to the conduit 14 near the entry port 16 is shown. A cover 12' that has a tab 19' for ease of handling is also shown covering access channel 26, and may be a pierceable cover 12, is better seen in FIG. 5B. Assay chamber 13 is in fluidic contact with entry port 16 (via interior channel 22) and with assay port 17 via access channel 26. In the embodiments shown in FIGS. 5A-5B, assay port 17 is occluded by a stopper 23 with needle 28; fluidic access to assay chamber 13 is via needle 28.

As indicated by the darker shading and the fill-lines shown in FIGS. 5A and 5B, an assay chamber 13 (and an access channel 26) may be at least partially filled with a reagent 25; such a reagent 25 may be a reagent for bathing a swab as discussed above (e.g., a transfer medium, saline, distilled water, or other reagent). Thus, a reagent 25 may aid in releasing sample material from the swab for analysis. Such release of sample material into a reagent 25 provides fluid containing sample material which may be used for sample analysis. Access to the reagent 25 containing a sample obtained from a swab 24 may be via assay port 17 and access channel 26. An access channel 26 may have a needle 28 positioned therein, as shown in FIGS. 5A and 5B. In embodiments, access to the reagent 25 containing a sample obtained from a swab 24 may be by way of a pipette, or suction tube, or capillary tube, or siphon, or other means. For example, a vial (e.g., a vial having a rubber cap or other pierceable cap) may be placed into access channel 26 and onto needle 28 for drawing fluid out of the assay chamber 13. Such a vial may, for example, have a partial or total vacuum prior to piercing a pierceable cap, effective that puncture of the vial's pierceable cap by needle 28 allows fluid from assay chamber 13 to be drawn into such a vial. A stand 29 may stabilize or otherwise aid in the use of a swab container 10 as shown in FIGS. 5A and 5B. The container may then be used to transport the fluid to a location or device for analysis, or the container itself may be used, at least in part, for analysis of the fluid.

FIG. 5A also shows contact angle 24 between assay chamber 13 and access channel 26. A contact angle 24 may be any suitable angle. In embodiments, a contact angle 24 may be between about 2° to about 90°. In embodiments, a contact angle 24 may be between about 5° to about 75°. In embodiments, a contact angle 24 may be between about 7° to about 40°. In embodiments, a contact angle 24 may be between about 10° to about 20°. In the embodiment shown in FIG. 5A, the contact angle is about 15°.

Figure 6:
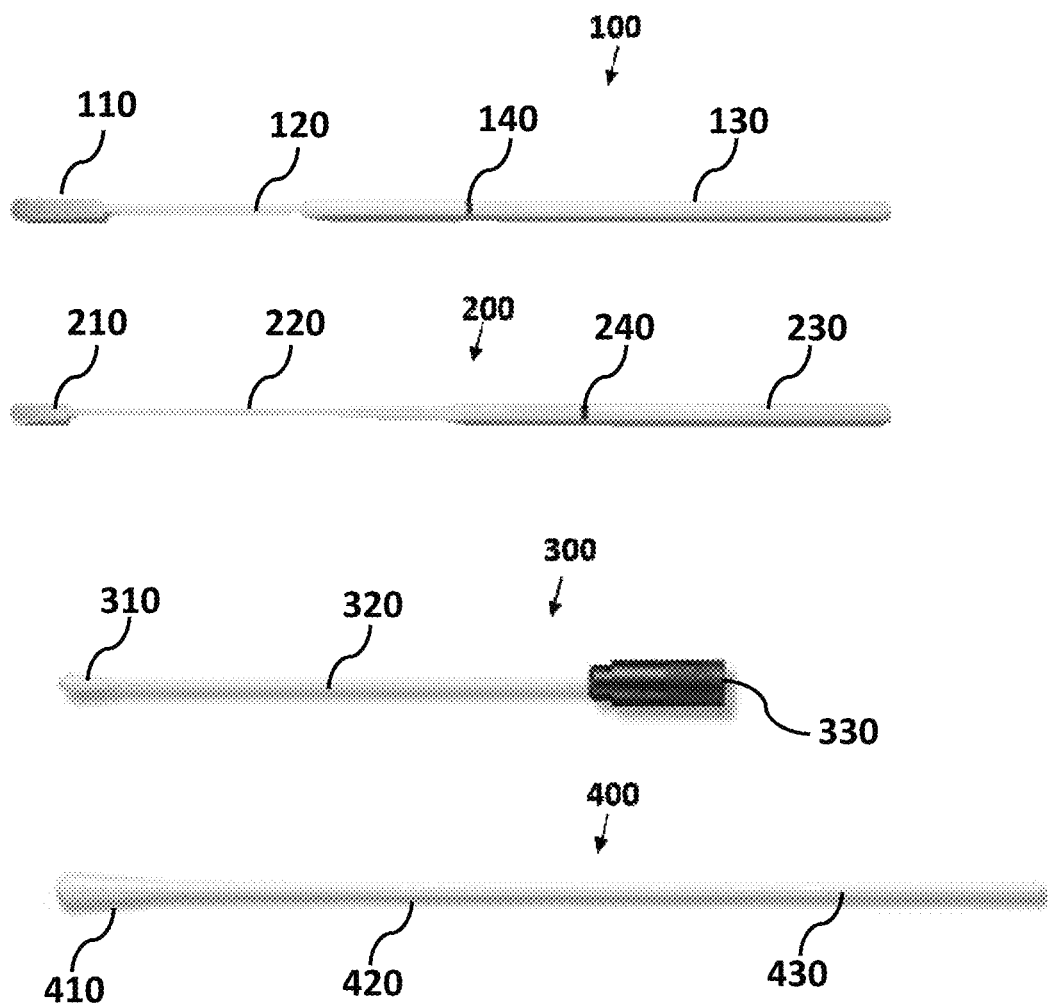
FIG. 6 shows examples of swabs which may be used to obtain samples from the throat, nasal passages, cheeks, or other body locations of subjects.

Swabs may be any suitable swab for collection of a sample. As shown in FIG. 6, swabs may have different kinds of tips; may have different kinds of handles; may have different lengths; and may have other differences. For example, swabs may be made of many different materials: for example, swab tips may be cotton, plastic, polymer, or other material or combination of materials; and swab handles may be wood, paper, plastic, polymer, or other material or combination of materials. Several examples of swabs suitable for use in sample collection are shown in FIG. 6. Such swabs, and other swabs, may be used to obtain samples from the throat, nasal passages, cheeks, or other body locations of subjects. Swabs with flocked tips (swab 100, and the shorter swab 200, suitable for pediatric use), or those also suitable for use in establishing cultures of material obtained by swabbing a body cavity or surface of a subject (swab 300), cotton-tipped swabs (swab 400), and other swabs may be used to collect a sample from a patient for use with the methods, systems, and devices disclosed herein. Swabs may include a portion, or position, configured for breakage (e.g., a place, typically along the handle, which is weaker, thinner, scored, or otherwise more liable to break when bent, twisted, or pulled) which provides a longer handle for use while obtaining a sample with the tip of the swab, while also allowing the swab to be shortened after a sample is obtained (e.g., to better fit within the interior channel of a conduit of a swab container as disclosed herein).

As shown in FIG. 6, swab tips 110, 210, 310, and 410, although similar, may differ in shape, length, and width as well as in material. Swab tips 110, 210, 310, and 410 are attached to shafts 120, 220, 320, and 420 respectively; the shafts are connected to, and are typically seamlessly integrated with, handles 130, 230, 330, and 430. Some swabs may include a break-point (e.g., swabs 100 and 200 include break-points 140 and 240, respectively) configured to allow easy shortening of a swab (which is useful, e.g., after sample collection) by breaking the shaft 120 or 220 at a break-point 140 or 240, in order to separate the shaft 120 or 220 from the handle portion 130 or 230.

Figure 7A:
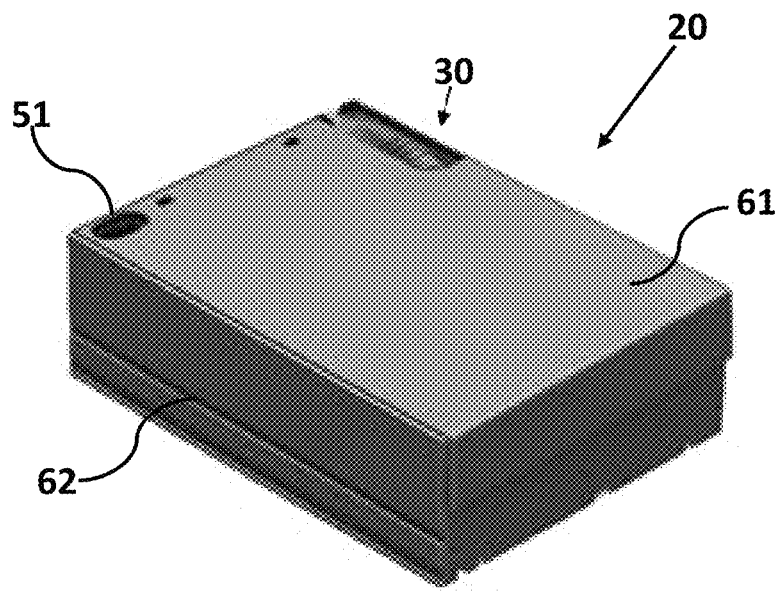
FIGS. 7A-7B show a cartridge having a cover and configured to accept a swab container.
Figure 7B:
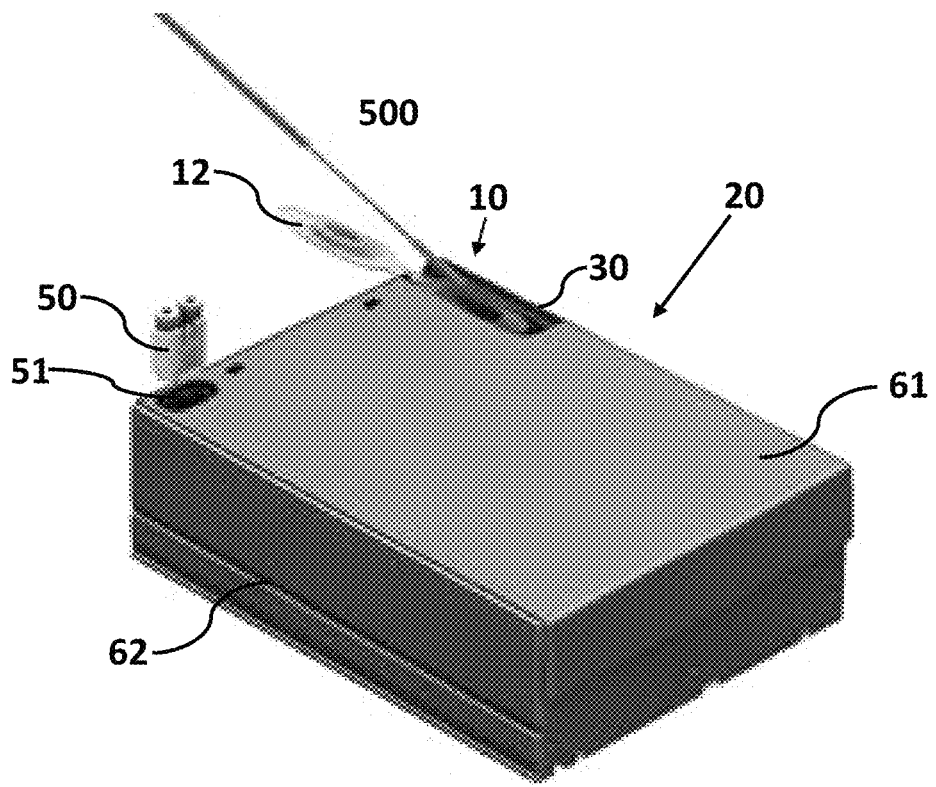

FIGS. 7A-7B show a cartridge 20 having a cover 61 and configured to accept a swab container. FIG. 7A shows such a cartridge 20 with its cover 61 closed, and with a swab container 10 in place in the swab container receptacle 30 (and the swab container cover 61 closed). FIG. 7B shows a swab 500 being placed into the swab container 10 (with its cover 12 open, to allow receipt of the swab 500 into entry port 16); a sample collection vessel 50 is also shown in position for placement into a sample collection vessel receptacle 51 in the cartridge 20. The cartridge 20 shown in FIGS. 7A and 7B has a guide 62 which is configured to aid in the proper placement of the cartridge 20 in a sample processing device or a sample analysis device, or other device or system which may receive the cartridge. A cartridge 20 may have a pair of guides, one on each of two opposite sides of the cartridge (e.g., a guide 62 as shown in FIGS. 7A and 7B, and a further guide in a similar or symmetric location on the opposite side (not shown in the figures). In embodiments, a cartridge 20 may have more than two such guides; for example, a cartridge 20 may have two pair of such guides. The guides 62 of FIGS. 7A and 7B are shown as slots; however, it will be understood that a guide 62, or a pair of guides 62, or a plurality of guides 62 may include slots (as shown), rails, slides, pegs, pins, and other elements. Such elements may be configured to slide into, or slide over, or to mate with, or otherwise operably engage complementary elements in or on a sample processing device or a sample analysis device, or other device or system which may receive the cartridge. In one non-limiting example, the guide can be "keyed" to have a specific cross-sectional shape such that cartridge 20 can only be received into the device in a specific orientation. Optionally, some embodiments, may have different shaped and/or sized features on each side of the cartridge 20 so that the orientation in which the cartridge in inserted can be controlled. Some embodiments may have this feature only along one surface of the cartridge. Some may have the feature along a lower or upper portion to minimize the risk that the cartridge is inserted upside-down. In this manner, a user is directed to insert the cartridge 20 in the correct manner.

Figure 8:
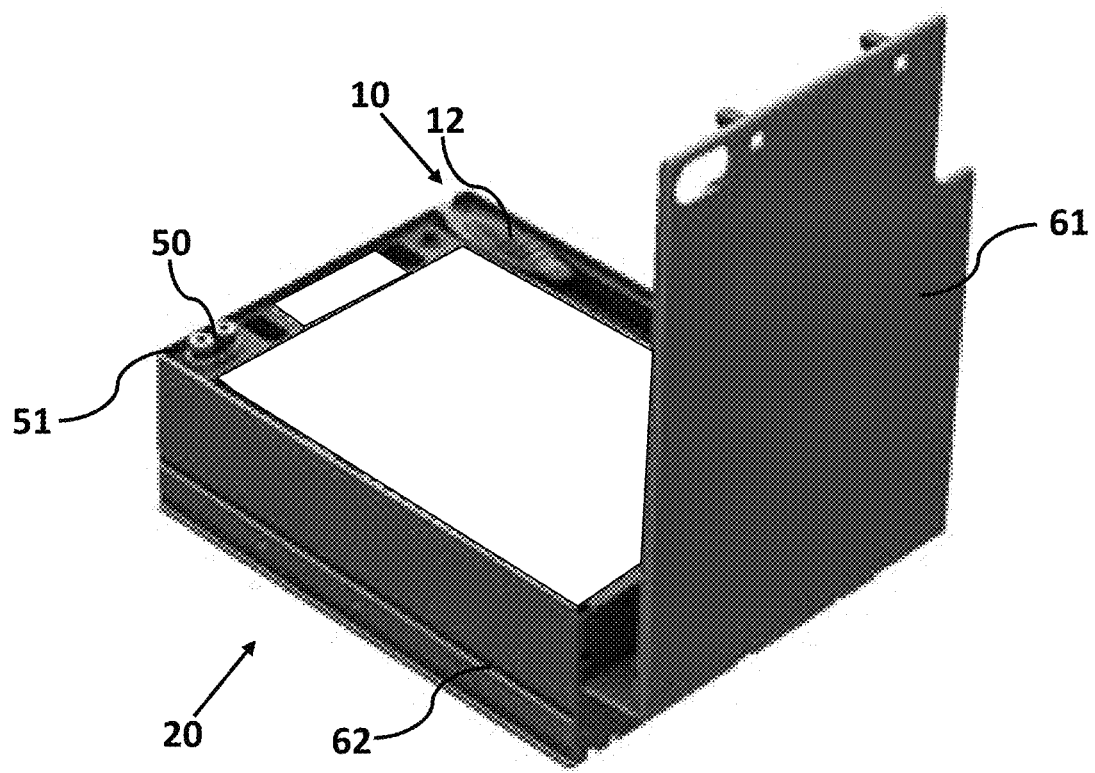
FIG. 8 shows a cartridge with its cover open; the cartridge has a swab container receptacle containing a (closed) swab container, and also contains a sample collection vessel in a sample collection vessel receptacle.

FIG. 8 shows a cartridge 20 with its cover 61 open; the cartridge 20 has a swab container receptacle 30 containing a swab container 10 (with its swab container lid 12 closed), and also contains a sample collection vessel 50 in a sample collection vessel receptacle 51.

Figure 9A:
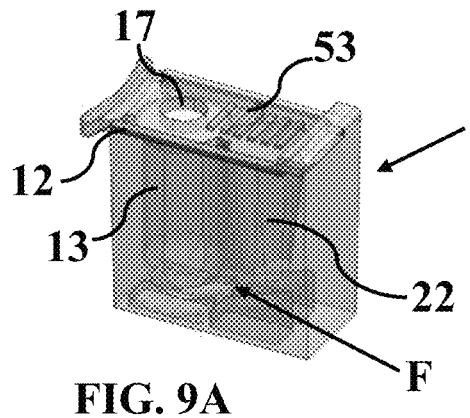
FIGS. 9A-9E show an embodiment of a swab container, illustrating several configurations during use.

FIGS. 9A-9E show an embodiment of a swab container 11, illustrating several configurations during use. FIG. 9A shows a closed swab container 11; in the closed configuration, the lid 12 covers entry port 16 leading to interior channel 22, but access to assay port 17 and thus to assay chamber 13 remains open. Interior channel 22 is in fluid communication with assay chamber 13 of the swab container 11, e.g., as indicated by the arrow F in FIGS. 9A and 9E (the arrows, and other indicator lines and numerals are not shown in all figures for simplicity of illustration, but indications in one figure may be used to identify similar features in other figures). A cover 12 of a swab container 11 may be configured for manual manipulation; for example, a cover 12 may have raised features 53, and may have a handle 55, as shown, which aid in engaging and moving a cover 12 by hand. In embodiments, a cover 12 may have depressions, or notches, or a raised shaft or shafts, or another feature or features configured to aid in its manual manipulation (e.g., to aid manual sliding of a cover 12 to open or closed configurations).

Figure 9B:
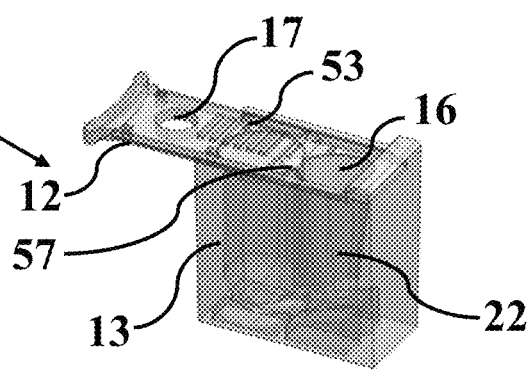

FIG. 9B shows an open swab container 11 with the cover 12 slid to expose entry port 16 leading to interior channel 22; in this configuration, cover 12 closes off assay port 17 and thus encloses the outer portion of assay chamber 13.

Figure 9C:
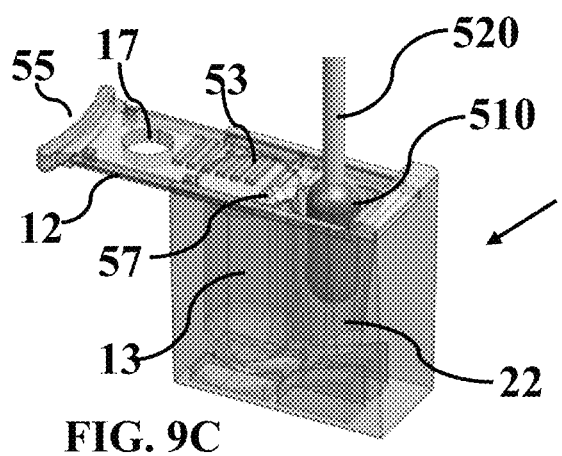

FIG. 9C shows an open swab container 11 with a swab 500 having a swab tip 510 and a swab shaft 520, the swab tip 510 being partially inserted into the interior channel 22 of the swab container 11.

Figure 9D:
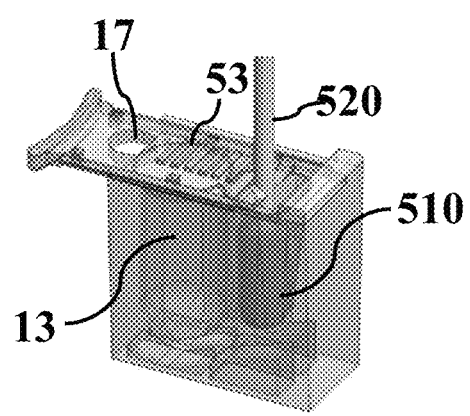

FIG. 9D shows the swab container 11 with its cover 12 partially closed. The cover 12 has sharp edges 57 in position and ready to sever the shaft 520 of a swab 500 that is in place with swab tip 510 and a portion of swab shaft 520 within the interior channel 22.

Figure 9E:
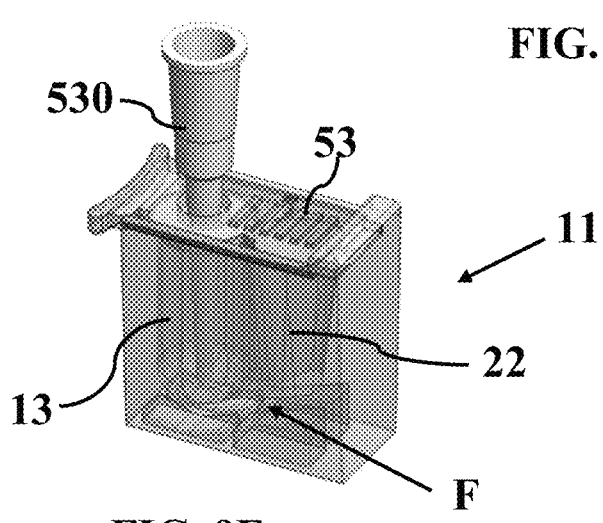

FIG. 9E shows a swab container 11 in a closed configuration with a pipette 520 in place in the assay chamber 13 (via assay port 17). Interior channel 22 is in fluid communication with assay chamber 13; thus, when a reagent (e.g., a reagent for bathing a swab) is present in interior channel 22, a pipette 530 inserted into an assay chamber 13 via assay port 17 is in position to remove at least a portion of the reagent. A reagent removed by a pipette 530 may include, for example, sample material obtained from a subject; the interior channel 22 may have held a reagent that had bathed a swab tip 510 after the swab tip 510 had contacted a subject (e.g., had contacted a subject's nasal passages or other portion of a subject).

In embodiments, an interior channel 22 and an assay chamber 13 may be at least partially filled with a reagent for bathing a swab prior to placement of a swab tip 510 in an interior channel 22. In embodiments, a pipette 530 may carry or otherwise provide a reagent and may be used to at least partially fill an assay chamber 13 (and thus to at least partially fill an interior channel 22 which is in fluid communication with the assay chamber 13). In embodiments, such filling may be, e.g., prior to placement of a swab tip 510 within the interior channel 22. In embodiments, such filling may be, e.g., after placement of a swab tip 510 within the interior channel 22.

Figure 10:
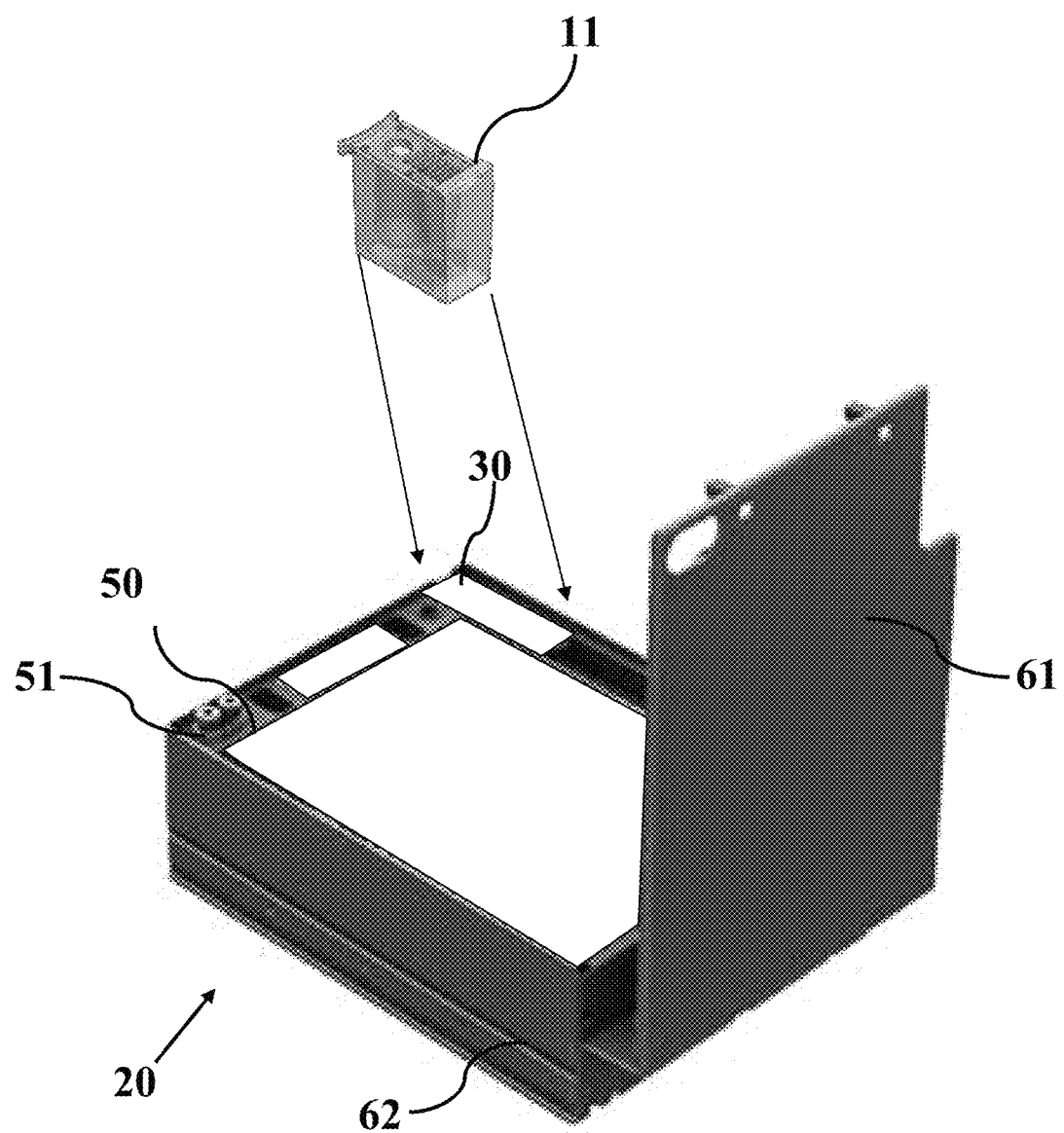
FIG. 10 shows an example of a cartridge with its cover open, showing a swab container and indicating that the swab container can fit into the swab container receptacle as illustrated.

FIG. 10 shows an example of a cartridge 20 with its cover 61 open, showing a swab container 11 and indicating that the swab container 11 can fit into the swab container receptacle 30 as illustrated. A sample collection vessel 50 is also shown in place in a sample collection vessel receptacle 51.

Figure 11:
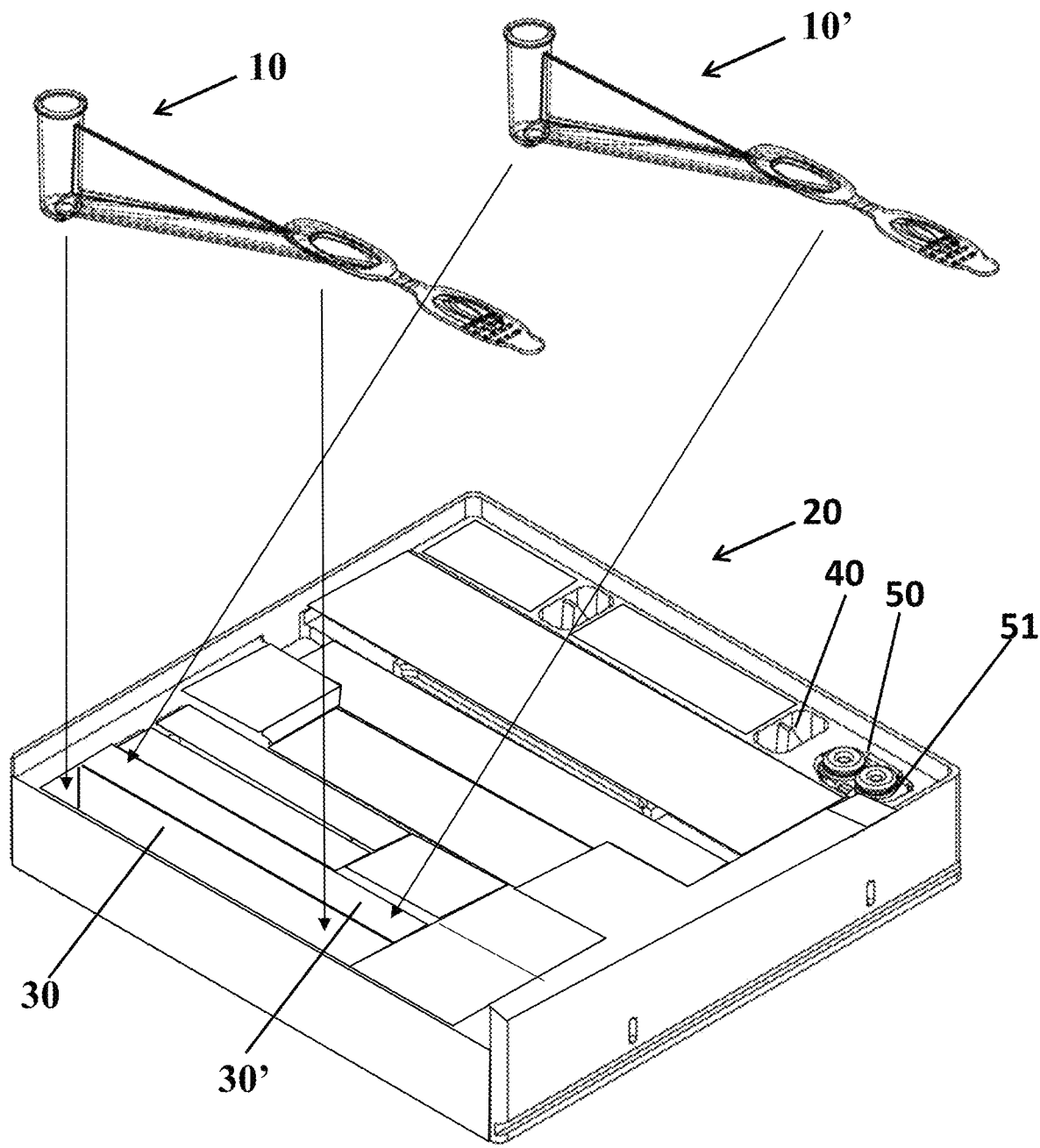
FIG. 11 shows an example of a cartridge having two swab container receptacles, and indicating that each of the swab containers shown can fit into a swab container receptacle as illustrated.

FIG. 11 shows an example of a cartridge 20' having two swab container receptacles 30 and 30', and indicating that each of the swab containers 10 and 10' can each fit into a swab container receptacle (either 30 or 30'). Other receptacles (e.g., 40) may hold other vessels and containers (e.g., a sample collection vessel 50 in a sample collection vessel receptacle 51 as shown) or may be configured to hold fluids or other materials in the absence of a vessel or other container. It will be understood that, in further embodiments, a cartridge may include a single swab container receptacle that is configured to hold two swab containers. In yet further embodiments, a cartridge may include a single swab container receptacle that is configured to hold three, or more, swab containers.

Devices for use in performing assays for detecting one or a plurality of disease-causing agents as disclosed herein. In embodiments, such devices for use in performing assays for detecting one or a plurality of disease-causing agents comprise cartridges, wherein the cartridges may further a space, or a container, for holding a swab (e.g., may include a receptacle configured to receive and retain a swab container, and may include a swab container in the receptacle). Thus, in embodiments, a cartridge may be configured to hold a swab container; the swab container may include a swab held therein, or may be empty of a swab (e.g., may be ready to receive a swab. In embodiments, a cartridge may include one, two, or more space(s) for holding two swabs, or a plurality of swabs, where such a space or spaces may include one or more receptacle(s) configured to receive and retain a swab container, or a plurality of swab containers, and may include a swab container or a plurality of swab containers in the receptacle or receptacles. In embodiments, a single swab may be placed in a single space, or a single swab container; in embodiments, two swabs may be placed in a single space, or single swab container; and in embodiments, a plurality of swabs may be placed in a single space, or single swab container. In embodiments, a plurality of swabs may be placed in a plurality of spaces, or in a plurality of swab containers. Such a swab container, or such swab containers, may contain a reagent, or a diluent, or other solution for use with a swab or swabs. Thus, in embodiments, a swab container may be prepared for use by including an amount of reagent, such as, e.g., a reagent for bathing a swab, within the swab container. In embodiments, a reagent for bathing a swab may be disposed within an assay chamber of a swab container. In embodiments, a reagent for bathing a swab may be disposed within an interior channel of a swab container. In embodiments, a reagent for bathing a swab may be disposed within an assay chamber and within an interior channel of a swab container.

In embodiments, a cartridge for use in performing assays for detecting one or a plurality of disease-causing agents may include a swab container. In embodiments, a cartridge for use in performing assays for detecting one or a plurality of disease-causing agents may include a swab container, and may further include a swab. A swab included in a cartridge may be an unused swab, ready for use in collecting a sample form a subject. In embodiments, a cartridge may carry a swab (e.g., within a swab container) after the swab has been used to collect a sample from a subject; for example, after collection, a swab may be placed within a swab container, and the swab container placed in a receptacle in a cartridge. Such a cartridge may then be placed in a sample processing device, an analysis device, or other device or system for processing and analysis.

For example, a throat swab or a nasal swab may be used to collect a sample from the throat or nasal passage of a subject. A nasal swab may be useful for testing for upper respiratory diseases, and a throat swab may be useful for testing lower respiratory diseases. In embodiments, the throat swab or the nasal swab may be placed in a swab container, and the swab container may be placed in a cartridge. The swab container may contain a reagent, or a diluent, or other solution for use with the swab. The cartridge may be placed in a sample processing device, an analysis device, or other device or system, for processing and/or analysis. Such processing and analysis devices and systems may be located at the same location as the location in which the sample was obtained; or such devices and systems may be located at a different location or locations than the one at which the sample was obtained.

For example, both a throat swab and a nasal swab may be used to collect a sample from the throat and from a nasal passage of a subject. In embodiments, the throat swab may be placed in one cartridge, and the nasal swab may be placed in a different cartridge. In embodiments, the cartridge may have two or more interior channels; in such embodiments, the throat swab may be placed in one interior channel of a cartridge, and the nasal swab may be placed in a different interior channel of that cartridge. The swab container may contain a reagent, or a diluent, or other solution for use with the swabs; such reagents may be different for the throat swab and the nasal swab. In embodiments, reagent for use with a throat swab may be held within the interior channel containing the throat swab, and reagent for use with a nasal swab may be held within the interior channel containing the nasal swab. The cartridge may be placed in a sample processing device, an analysis device, or other device or system, for processing and/or analysis. Such processing and analysis devices and systems may be located at the same location as the location in which the sample was obtained; or such devices and systems may be located at a different location or locations than the one at which the sample was obtained.

In embodiments, a cartridge may be configured to contain a reagent vessel or a plurality of reagent vessels. In embodiments, a cartridge may be configured to contain a mixing vessel or a plurality of mixing vessels. In embodiments, a cartridge may be configured to contain an assay unit, or a plurality of assay units. In embodiments, a cartridge may be configured to contain an implement, or a plurality of implements, where the implement may be one or more of a cuvette (e.g., a cytometry cuvette), or a magnet (e.g., a magnetic bar); or other tool or device. In embodiments, a cartridge may be configured to contain a waste container, or a plurality of waste containers. In embodiments, a cartridge may be configured to contain a sample collection vessel. In embodiments, a cartridge may be configured to contain a sample; in embodiments, a sample may be contained in a sample collection vessel. In embodiments, a cartridge may be configured to contain a pipette tip, or a plurality of pipette tips. In embodiments, a cartridge may be configured to contain a transport unit, or a plurality of transport units.

In embodiments, a cartridge configured to hold a swab container, or holding a swab container, may be configured to contain a reagent vessel, or a plurality of reagent vessels, and a mixing vessel or a plurality of mixing vessels. In embodiments, a cartridge configured to hold a swab container, or holding a swab container, may be configured to contain a reagent vessel, or a plurality of reagent vessels, and an assay unit, or a plurality of assay units. In embodiments, a cartridge configured to hold a swab container, or holding a swab container, may be configured to contain an assay unit, or a plurality of assay units, and a mixing vessel or mixing vessels. In embodiments, a cartridge configured to hold a swab container, or holding a swab container, may be configured to contain a reagent vessel, or a plurality of reagent vessels, a mixing vessel or mixing vessels, and an assay unit, or a plurality of assay units. In embodiments, a cartridge configured to hold a swab container, or holding a swab container, may be configured to hold an implement. In embodiments, a cartridge configured to hold a swab container, or holding a swab container, may be configured to hold a waste container. In embodiments, a cartridge configured to hold a swab container, or holding a swab container, may include a touch-off pad. It will be understood that a cartridge configured to hold a reagent vessel, or assay unit, or mixing vessel, or implement, or waste container, may hold such a reagent vessel, or assay unit, or mixing vessel, or implement, or waste container. It will be understood that any or all of such cartridges may be configured to contain, and may contain, a pipette tip, or a plurality of pipette tips. It will be understood that any or all of such cartridges may be configured to contain, and may contain, a transport unit, or a plurality of transport units.

In embodiments, such a cartridge may include reagents for use in nucleic acid assays; for amino acid assays (e.g., ELISA assays); general chemistry assays (e.g., for clinical electrolytes, vitamin levels, blood component levels, and other targets); cytometric assays; and for combinations thereof. In embodiments, such a cartridge may include reagents for bathing a swab. In embodiments, such a cartridge may include a swab container which contains a reagent, or reagents, for bathing a swab. In embodiments, such a cartridge may include reagents for bathing a swab, and other reagents, vessels, assay units, pipette tips, transport units, implements, and combinations thereof. In embodiments, such a cartridge may include reagents and mixing vessels for use in nucleic acid assays; for amino acid assays (e.g., ELISA assays); general chemistry assays (e.g., for clinical electrolytes, vitamin levels, blood component levels, and other targets); cytometric assays; and for combinations thereof. In embodiments, such a device may include reagents, mixing vessels, assay units, pipette tips, transport units, and tools, cuvettes, and other implements for use in nucleic acid assays; for amino acid assays (e.g., ELISA assays); general chemistry assays (e.g., for clinical electrolytes, vitamin levels, blood component levels, and other targets); cytometric assays; and for combinations thereof.

Kits

Kits including a swab container as disclosed herein are disclosed, where the swab container may be any swab container disclosed herein. Kits including a swab container as disclosed herein, and a swab, are disclosed, where the swab container may be any swab container disclosed herein. In embodiments, a kit may include a cartridge configured to hold a swab container, and a swab container, where the swab container may be any swab container disclosed herein and the cartridge may be any cartridge disclosed herein. In embodiments, a kit may include a cartridge configured to hold a swab container, a swab, and a swab container, where the swab container may be any swab container disclosed herein and the cartridge may be any cartridge disclosed herein. For example, in embodiments, a kit may include a cartridge configured to hold a swab container, and a swab container, wherein the swab container contains a reagent therein. For example, in embodiments, a kit may include a cartridge configured to hold a swab container, a swab, and a swab container, wherein the swab container contains a reagent therein. For example, in embodiments, a kit may include a cartridge configured to hold a swab container, a reagent vessel, and a swab container. For example, in embodiments, a kit may include a cartridge configured to hold a swab container, a reagent vessel, a swab, and a swab container.

For example, in embodiments, a kit may include a cartridge configured to hold a swab container, and a swab container, and one or more of a mixing vessel, a reagent vessel, an assay unit, a pipette tip, a transport unit, an implement, and a waste container. For example, in embodiments, a kit may include a cartridge configured to hold a swab container, a swab, and a swab container, and one or more of a mixing vessel, a reagent vessel, an assay unit, a pipette tip, a transport unit, an implement, and a waste container.

Sample Processing Device

In embodiments, a cartridge may be provided in a sample processing device. A device may be part of a system, a component of which may be a sample processing device. A device may be a sample processing device. A sample processing device may be configured to facilitate collection of a sample, prepare a sample for a clinical test, or effect a chemical reaction with one or more reagents or other chemical or physical processing, as disclosed herein. A sample processing device may be configured to obtain data from a sample. A sample processing device may be configured to transmit data obtained from a sample. A sample processing device may be configured to analyze data from a sample. A sample processing device may be configured to communicate with another device, or a laboratory, or an individual affiliated with a laboratory, to analyze data obtained from a sample.

A sample processing device may receive a sample from the subject through a housing of the device. The sample collection may occur at a sample collection site, or elsewhere. The sample may be provided to the device at a sample collection site.

In some embodiments, a sample processing device may be configured to accept or hold a cartridge. In some embodiments, a sample processing device may comprise a cartridge. The cartridge may be removable from the sample processing device. In some embodiments, a sample may be provided to the cartridge of the sample processing device.

Alternatively, a sample may be provided to another portion of a sample processing device. The cartridge and/or device may comprise a sample collection unit that may be configured to accept a sample.

A cartridge may include a sample, and may include reagents for use in processing or testing a sample, disposables for use in processing or testing a sample, or other materials. Following placement of a cartridge on, or insertion of a cartridge into, a sample processing device, one or more components of the cartridge may be brought into fluid communication with other components of the sample processing device. For example, if a sample is collected at a cartridge, the sample may be transferred to other portions of the sample processing device. Similarly, if one or more reagents are provided on a cartridge, the reagents may be transferred to other portions of the sample processing device, or other components of the sample processing device may be brought to the reagents. In some embodiments, the reagents or components of a cartridge may remain on-board the cartridge. In some embodiments, no fluidics are included that require tubing or that require maintenance (e.g., manual or automated maintenance).

A sample or reagent may be transferred to a device, such as a sample processing device. A sample or reagent may be transferred within a device. Such transfer of sample or reagent may be accomplished without providing a continuous fluid pathway from cartridge to device. Such transfer of sample or reagent may be accomplished without providing a continuous fluid pathway within a device. In embodiments, such transfer of sample or reagent may be accomplished by a sample handling system (e.g., a pipette); for example, a sample, reagent, or aliquot thereof may be aspirated into an open-tipped transfer component, such as a pipette tip, which may be operably connected to a sample handling system which transfers the tip, with the sample, reagent, or aliquot thereof contained within the tip, to a location on or within the sample processing device. The sample, reagent, or aliquot thereof can be deposited at a location on or within the sample processing device. Sample and reagent, or multiple reagents, may be mixed using a sample handling system in a similar manner. One or more components of the cartridge may be transferred in an automated fashion to other portions of the sample processing device, and vice versa.

A device, such as a sample processing device, may have a fluid handling system (also termed herein a sample handling system). A fluid handling system may perform, or may aid in performing, transport, dilution, extraction, aliquotting, mixing, and other actions with a fluid, such as a sample. In some embodiments, a fluid handling system may be contained within a device housing. A fluid handling system may permit the collection, delivery, processing and/or transport of a fluid, dissolution of dry reagents, mixing of liquid and/or dry reagents with a liquid, as well as collection, delivery, processing and/or transport of non-fluidic components, samples, or materials. The fluid may be a sample, a reagent, diluent, wash, dye, or any other fluid that may be used by the device, and may include, but not limited to, homogenous fluids, different liquids, emulsions, suspensions, and other fluids. A fluid handling system, including without limitation a pipette, may also be used to transport vessels (with or without fluid contained therein) around the device. The fluid handling system may dispense or aspirate a fluid. The sample may include one or more particulate or solid matter floating within a fluid.

In embodiments, a fluid handling system may comprise a pipette, pipette tip, syringe, capillary, or other component. The fluid handling system may have portion with an interior surface and an exterior surface and an open end. The fluid handling system may comprise a pipette, which may include a pipette body and a pipette nozzle, and may comprise a pipette tip. A pipette tip may or may not be removable from a pipette nozzle. In embodiments, a fluid handling system may use a pipette mated with a pipette tip; a pipette tip may be disposable. A tip may form a fluid-tight seal when mated with a pipette. A pipette tip may be used once, twice, or more times. In embodiments, a fluid handling system may use a pipette or similar device, with or without a pipette tip, to aspirate, dispense, mix, transport, or otherwise handle the fluid. The fluid may be dispensed from the fluid handling system when desired. The fluid may be contained within a pipette tip prior to being dispensed, e.g., from an orifice in the pipette tip. In embodiments, or instances during use, all of the fluid may be dispensed; in other embodiments, or instances during use, a portion of the fluid within a tip may be dispensed. A pipette may selectively aspirate a fluid. The pipette may aspirate a selected amount of fluid. The pipette may be capable of actuating stirring mechanisms to mix the fluid within the tip or within a vessel. The pipette may incorporate tips or vessels creating continuous flow loops for mixing, including of materials or reagents that are in non-liquid form. A pipette tip may also facilitate mixture by metered delivery of multiple fluids simultaneously or in sequence, such as in 2-part substrate reactions.

A fluid handling system may include one or more fluidically isolated or hydraulically independent units. For example, the fluid handling system may include one, two, or more pipette tips. The pipette tips may be configured to accept and confine a fluid. The tips may be fluidically isolated from or hydraulically independent of one another. The fluid contained within each tip may be fluidically isolated or hydraulically independent from one fluids in other tips and from other fluids within the device. The fluidically isolated or hydraulically independent units may be movable relative to other portions of the device and/or one another. The fluidically isolated or hydraulically independent units may be individually movable. A fluid handling system may comprise one or more base or support. A base or support may support one or more pipette or pipette units. A base or support may connect one or more pipettes of the fluid handling system to one another.

A sample processing device may be configured to perform processing steps or actions on a sample obtained from a subject. Sample processing may include sample preparation, including, e.g., sample dilution, division of a sample into aliquots, extraction, contact with a reagent, filtration, separation, centrifugation, or other preparatory or processing action or step. A sample processing device may be configured to perform one or more sample preparation action or step on the sample. In embodiments, a sample may be prepared for a chemical reaction and/or physical processing step. A sample preparation action or step may include one or more of the following: centrifugation, separation, filtration, dilution, enriching, purification, precipitation, incubation, pipetting, transport, chromatography, cell lysis, cytometry, pulverization, grinding, activation, ultrasonication, micro column processing, processing with magnetic beads, processing with nanoparticles, or other sample preparation action or steps. For example, sample preparation may include one or more step to separate a sample into various components. Sample preparation may include one or more step to dilute and/or concentrate a sample, such as a biological sample, e.g., of material obtained from a nasal swab, a throat swab, a cheek swab, or other sample, or other biological samples. Sample preparation may include adding an anti-coagulant or other ingredients to a sample. Sample preparation may also include purification of a sample. In embodiments, all sample processing, preparation, or assay actions or steps are performed by a single device. In embodiments, all sample processing, preparation, or assay actions or steps are performed within a housing of a single device. In embodiments, most sample processing, preparation, or assay actions or steps are performed by a single device, and may be performed within a housing of a single device. In embodiments, many sample processing, preparation, or assay actions or steps are performed by a single device, and may be performed within a housing of a single device. In embodiments, sample processing, preparation, or assay actions or steps may be performed by more than one device.

A sample processing device may be configured to run one or more assay on a sample, and to obtain data from the sample. An assay may include one or more physical or chemical treatments, and may include running one or more chemical or physical reactions. A sample processing device may be configured to perform one, two or more assays on a small sample of bodily fluid. One or more chemical reaction may take place on a sample having a volume, as described elsewhere herein. For example one or more chemical reaction may take place in a pill having less than femtoliter volumes. In an instance, the sample collection unit is configured to receive a volume of the bodily fluid sample equivalent to a single drop or less of blood or interstitial fluid. In embodiments, the volume of a sample may be a small volume, where a small volume may be a volume that is less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. In embodiments, all sample assay actions or steps are performed on a single sample. In embodiments, all sample assay actions or steps are performed by a single device. In embodiments, all sample assay actions or steps are performed within a housing of a single device. In embodiments, most sample assay actions or steps are performed by a single device, and may be performed within a housing of a single device. In embodiments, many sample assay actions or steps are performed by a single device, and may be performed within a housing of a single device. In embodiments, sample processing, preparation, or assay actions or steps may be performed by more than one device.

A sample processing device may be configured to perform a plurality of assays on a sample. For example, a sample processing device may be configured to detect, or to identify, or to measure pathogen-identifying material in a sample. In embodiments, a sample processing device may be configured to perform a plurality of assays on a single sample. In embodiments, a sample processing device may be configured to perform a plurality of assays on a single biological sample, where the biological sample is a small sample. For example, a small sample may have a sample volume that is a small volume of less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. A sample processing device may be capable of performing multiplexed assays on a single sample. A plurality of assays may be run simultaneously; may be run sequentially; or some assays may be run simultaneously while others are run sequentially. One or more control assays and/or calibrators (e.g., including a configuration with a control of a calibrator for the assay/tests) can also be incorporated into the device; control assays and assay on calibrators may be performed simultaneously with assays performed on a sample, or may be performed before or after assays performed on a sample, or any combination thereof. In embodiments, all sample assay actions or steps are performed by a single device. In embodiments, all of a plurality of assay actions or steps are performed within a housing of a single device. In embodiments, most sample assay actions or steps, of a plurality of assays, are performed by a single device, and may be performed within a housing of a single device. In embodiments, many sample assay actions or steps, of a plurality of assays, are performed by a single device, and may be performed within a housing of a single device. In embodiments, sample processing, preparation, or assay actions or steps may be performed by more than one device.

In embodiments, all of a plurality of assays may be performed in a short time period. In embodiments, such a short time period comprises less than about three hours, or less than about two hours, or less than about one hour, or less than about 40 minutes, or less than about 30 minutes, or less than about 25 minutes, or less than about 20 minutes, or less than about 15 minutes, or less than about 10 minutes, or less than about 5 minutes, or less than about 4 minutes, or less than about 3 minutes, or less than about 2 minutes, or less than about 1 minute, or other short time period.

A sample processing device may be configured to detect one or more signals relating to the sample. A sample processing device may be configured to identify one or more properties of the sample. For instance, the sample processing device may be configured to detect the presence or concentration of one analyte or a plurality of analytes or a disease condition in the sample (e.g., in or through a bodily fluid, secretion, tissue, or other sample). Alternatively, the sample processing device may be configured to detect a signal or signals that may be analyzed to detect the presence or concentration of one or more analytes (which may be indicative of a disease condition) or a disease condition in the sample. The signals may be analyzed on board the device, or at another location. Running a clinical test may or may not include any analysis or comparison of data collected.

A chemical reaction or other processing step may be performed, with or without the sample. Examples of steps, tests, or assays that may be prepared or run by the device may include, but are not limited to immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and/or other types of assays, centrifugation, separation, filtration, dilution, enriching, purification, precipitation, pulverization, incubation, pipetting, transport, cell lysis, or other sample preparation action or steps, or combinations thereof. Steps, tests, or assays that may be prepared or run by the device may include imaging, including microscopy, cytometry, and other techniques preparing or utilizing images. Steps, tests, or assays that may be prepared or run by the device may further include an assessment of histology, morphology, kinematics, dynamics, and/or state of a sample, which may include such assessment for cells.

A device may be capable of performing all on-board steps (e.g., steps or actions performed by a single device) in a short amount of time. A device may be capable of performing all on-board steps on a single sample in a short amount of time. For example, from sample collection from a subject to transmitting data and/or to analysis may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less. The amount of time from accepting a sample within the device to transmitting data and/or to analysis from the device regarding such a sample may depend on the type or number of steps, tests, or assays performed on the sample. The amount of time from accepting a sample within the device to transmitting data and/or to analysis from the device regarding such a sample may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, it should be understood that the embodiments herein may be described in the context of a weightless environment, the small volume containers and their related methods are not limited to such environments and may find use in other environments such as but not limited to terrestrial environments under non-weightless conditions.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, and the like.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are fully incorporated herein by reference for all purposes:

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2013-2014 Theranos, Inc.

What is claimed is:

1. A cartridge for holding reagents comprising:
   at least one cartridge frame, and
   a swab container,
   wherein said cartridge frame is configured to receive a swab container; and wherein said swab container is configured to receive a swab, said swab container comprising:
      an entry port configured to receive the swab having a handle;
      an assay chamber having an assay port, said assay chamber being configured to receive a swab;
      a conduit comprising an interior channel connecting said entry port with said assay chamber, said conduit being configured to accept at least a portion of said swab handle therein; wherein said conduit provides fluidic communication between said entry port and said assay chamber effective that passing said swab through said entry port into said conduit allows a swab to be placed within said assay chamber to contain more than half of the handle of the swab in said conduit.

2. The cartridge of claim 1, wherein said assay chamber of said swab container contains a reagent for bathing a swab, wherein said reagent for bathing a swab is effective to receive sample material from said swab into said reagent.

3. The cartridge of claim 1, wherein said cartridge frame is configured to receive a vessel, an assay unit, a pipette tip, a transport unit, an implement, or combinations thereof.

4. The cartridge of claim 3, wherein said vessel comprises one or more of a reagent vessel, a mixing vessel, a waste vessel, and a sample collection vessel.

5. The cartridge of claim 3, wherein said vessel comprises a reagent vessel containing a reagent.

6. The cartridge of claim 3, wherein said implement comprises a cuvette or a magnet.

7. The cartridge of claim 1, wherein said swab container comprises a cover configured to cover said entry port, a cover configured to cover said assay port, or both.

8. The cartridge of claim 7, comprising a cover that is a pierceable cover.

9. The cartridge of claim 7, comprising a cover that is flexibly connected to said swab container.

10. The cartridge of claim 1, wherein said swab container comprises a conduit having a plurality of interior channels or a plurality of conduits each of which comprise at least one interior channel.

11. The cartridge of claim 1, wherein said swab container comprises a cover configured to cover said entry port, a cover configured to cover said assay port, or both.

12. The cartridge of claim 11, comprising a cover that is a pierceable cover.

13. The cartridge of claim 11, comprising a cover that is flexibly connected to said swab container.

14. The cartridge of claim 1, wherein said swab container comprises a conduit interior channel configured to squeeze a portion of a swab placed in or through a portion of the conduit interior channel adjacent to said assay chamber.

15. A cartridge comprising:
a cartridge frame comprising a plurality of receptacles, wherein said receptacles comprise:
one or more receptacles selected from a receptacle configured to receive a sample collection vessel, a receptacle configured to receive a reagent vessel, a receptacle configured to receive an assay unit, a receptacle configured to receive a pipette tip, a receptacle configured to receive a transport unit, a receptacle configured to receive a mixing vessel, a receptacle configured to receive a waste vessel, and a receptacle configured to receive an implement; and
a swab container receptacle configured to receive a swab container;
wherein said swab container comprises an entry port, said entry port configured to receive a swab having a handle; an assay chamber having an assay port, said assay chamber being configured to receive at least a portion of a swab; and a conduit comprising an interior channel connecting said entry port with said assay chamber, said conduit being configured to accept a least a portion of said swab handle therein, wherein said conduit provides fluidic communication between said entry port and said assay chamber effective that passing a swab through said entry port into said conduit allows the swab to be placed within said assay chamber to contain more than half of the handle of the swab in said conduit.

16. The cartridge of claim 15, comprising a swab container disposed in said swab container receptacle.

17. The cartridge of claim 15, wherein said assay chamber of said swab container contains a reagent for bathing a swab, wherein said reagent for bathing a swab is effective to receive sample material from said swab into said reagent.

18. The cartridge of claim 17, further comprising one or more of a sample collection vessel, a reagent vessel, an assay unit, a pipette tip, a transport unit, a mixing vessel, a waste vessel, and an implement disposed in one or more receptacles.

19. The cartridge of claim 15, further comprising a reagent vessel and a reagent contained within said reagent vessel.

20. The cartridge of claim 15, further comprising an implement.

21. The cartridge of claim 20, wherein said implement is selected from a cuvette and a magnet.

22. A system comprising:
a swab;
a container for receiving a swab having an assay chamber, a conduit, and an entry port and being configured to receive at least a portion of said swab in said assay chamber; and
a reagent for bathing a swab disposed in said assay chamber, wherein said reagent for bathing a swab is effective to receive sample material from said swab into said reagent
wherein said conduit provides fluidic communication between said entry port and said assay chamber effective that passing said swab through said entry port into said conduit allows the swab to be placed within said assay chamber to contain more than half of the handle of the swab in said conduit.

23. The system of claim 22, further comprising a cartridge comprising at least one cartridge frame
wherein said cartridge frame is configured to receive said container.

24. The system of claim 23, wherein a reagent vessel, an assay unit, a pipette tip, a transport unit, a waste vessel, a mixing vessel, a sample collection vessel, an implement, or combinations thereof, is disposed in said cartridge.

25. The system of claim 24, comprising a reagent vessel, wherein said reagent vessel comprises a reagent therein.

26. The system of claim 24, comprising an implement, wherein said implement comprises a cuvette or a magnet.

27. The system of claim 22, further comprising a sample processing device.

* * * * *